(12) United States Patent
Dacso et al.

(10) Patent No.: US 8,996,088 B2
(45) Date of Patent: Mar. 31, 2015

(54) APPARATUS AND METHOD FOR IMPROVING TRAINING THRESHOLD

(71) Applicant: University of Houston System, Houston, TX (US)

(72) Inventors: Clifford C. Dacso, Bellaire, TX (US); Luca Pollonini, Manvel, TX (US)

(73) Assignee: University of Houston System, Houston, TX (US)

(*) Notice: Subject to any disclaimer, the term of this patent is extended or adjusted under 35 U.S.C. 154(b) by 0 days.

(21) Appl. No.: 13/651,173

(22) Filed: Oct. 12, 2012

(65) Prior Publication Data

US 2013/0096403 A1 Apr. 18, 2013

Related U.S. Application Data

(60) Provisional application No. 61/546,704, filed on Oct. 13, 2011.

(51) Int. Cl.
*A61B 5/1455* (2006.01)
(52) U.S. Cl.
CPC .......... *A61B 5/14551* (2013.01); *A61B 2503/10* (2013.01); *A61B 2505/09* (2013.01)
USPC ............................. 600/324; 600/310; 600/322
(58) Field of Classification Search
USPC .................................................. 600/300–344
See application file for complete search history.

(56) References Cited

U.S. PATENT DOCUMENTS

| 7,220,220 B2* | 5/2007 | Stubbs et al. .................... 482/72 |
| 2007/0203448 A1 | 8/2007 | Melker et al. |
| 2008/0027330 A1 | 1/2008 | Naghavi et al. |
| 2009/0105605 A1 | 4/2009 | Abreu |
| 2010/0009328 A1* | 1/2010 | Nadeau .......................... 434/247 |
| 2010/0298899 A1* | 11/2010 | Donnelly et al. ................. 607/6 |
| 2011/0181422 A1 | 7/2011 | Tran |

OTHER PUBLICATIONS

PCT International Search Report and Written Opinion; International Application No. PCT/US2012/060100; Mailed Mar. 20, 2013.

* cited by examiner

*Primary Examiner* — Eric Winakur
*Assistant Examiner* — Marjan Fardanesh
(74) *Attorney, Agent, or Firm* — Novak Druce Connolly Bove + Quigg LLP

(57) ABSTRACT

The present invention generally relates to a non-invasive biosensor device configured to measure physiological parameters of a subject. In one aspect, a method of determining a training threshold of a subject is provided. The method includes the step of detecting an oxygenation parameter of a tissue of the subject using Near InfraRed Spectroscopy (NIRS). The method further includes the step of processing the oxygenation parameter. Additionally, the method includes the step of determining the training threshold of the subject using the result of the processing. In another aspect, a biosensor device for determining a lactate threshold of a subject during exercise is provided. In a further aspect, a biosensor device for measuring parameters of a subject during exercise is provided.

22 Claims, 15 Drawing Sheets

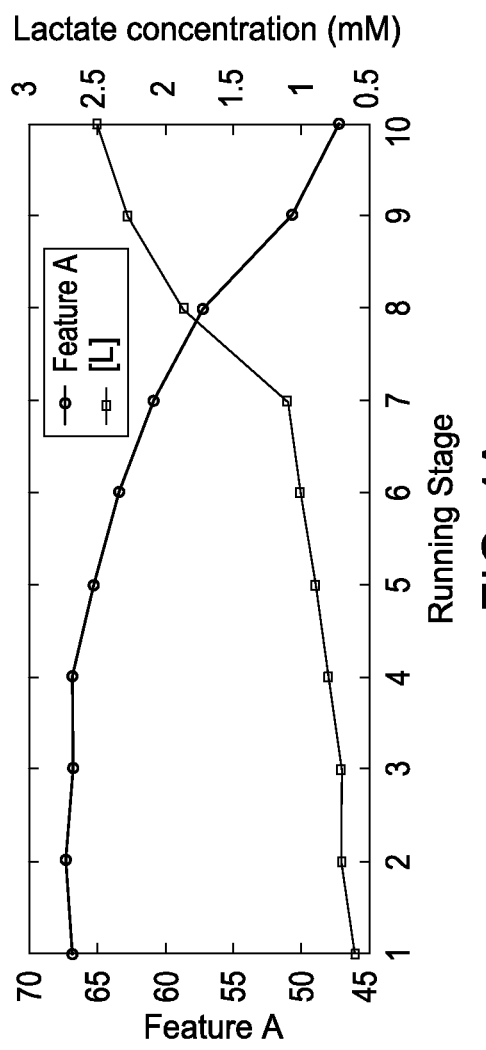
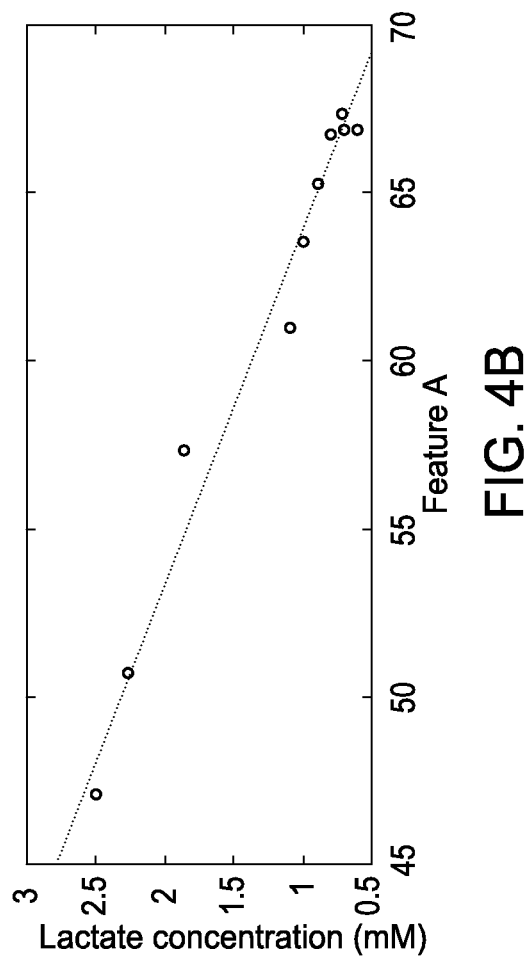
FIG. 4A
FIG. 4B

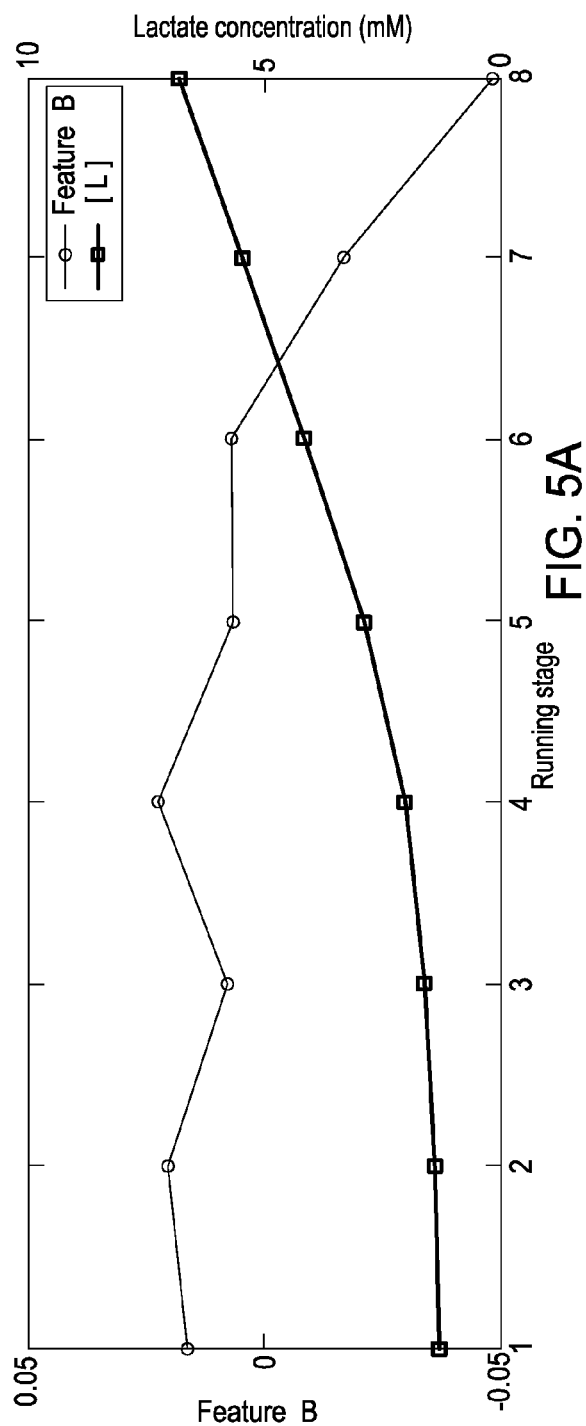
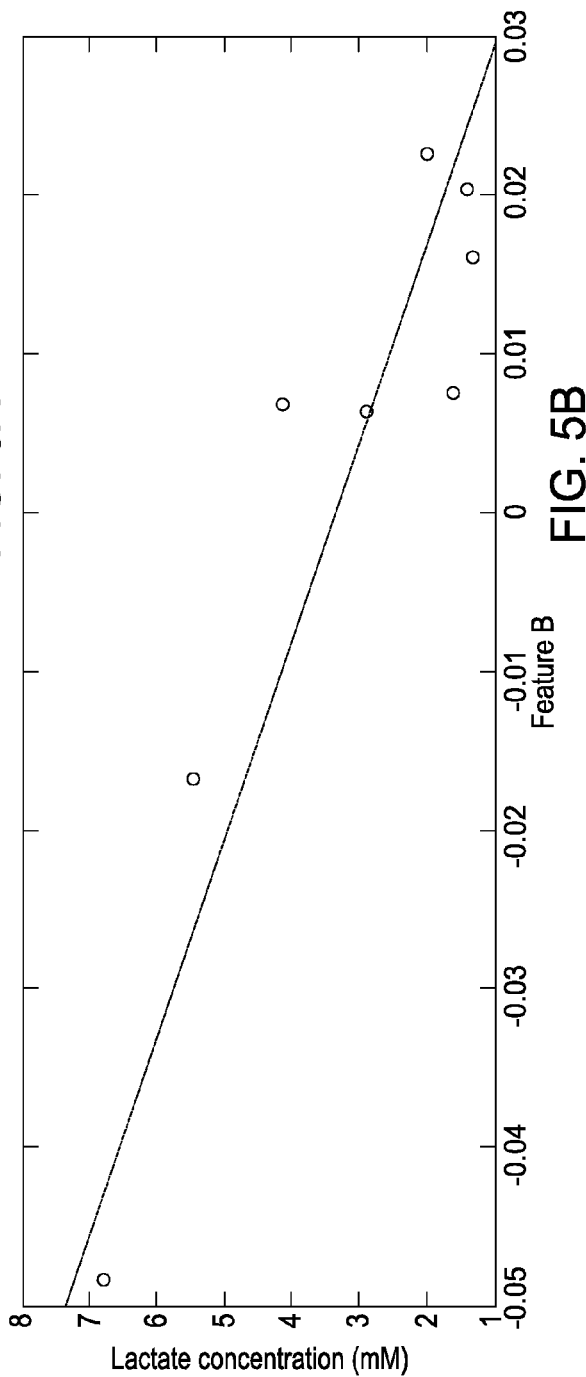
FIG. 5A
FIG. 5B

| Subject | Subject ID | Feature A | Feature B | Feature C | Feature D | Strong Correlation* |
|---|---|---|---|---|---|---|
| 1 | 2 | -0.94 | 0.06 | 0.85 | 0.19 | YES |
| 2 | 3 | -0.95 | -0.81 | 0.87 | 0.38 | YES |
| 3 | 5 | 0.51 | -0.45 | 0.73 | 0.68 | YES |
| 4 | 6 | -0.90 | -0.34 | 0.32 | -0.23 | YES |
| 5 | 7 | -0.91 | -0.32 | 0.92 | -0.70 | YES |
| 6 | 9 | -0.87 | -0.67 | 0.72 | 0.66 | YES |
| 7 | 10 | -0.09 | -0.86 | 0.84 | 0.87 | YES |
| 8 | 11 | 0.49 | -0.39 | 0.70 | 0.17 | YES |
| 9 | 12 | 0.60 | -0.92 | 0.79 | 0.79 | YES |
| 10 | 13 | 0.13 | -0.43 | 0.91 | 0.59 | YES |
| 11 | 14 | -0.86 | -0.50 | 0.75 | 0.09 | YES |
| 12 | 15 | -0.95 | -0.88 | 0.97 | 0.73 | YES |
| 13 | 16 | -0.47 | -0.26 | 0.18 | 0.67 | NO |
| 14 | 17 | -0.74 | -0.32 | 0.47 | 0.23 | YES |
| 15 | 18 | 0.18 | -0.89 | 0.24 | 0.41 | YES |
| 16 | 19 | -0.25 | -0.75 | 0.45 | 0.95 | YES |
| 17 | 20 | -0.87 | -0.57 | 0.75 | 0.75 | YES |
| 18 | 21 | -0.86 | -0.08 | 0.83 | 0.18 | YES |
| 19 | 22 | -0.81 | -0.64 | 0.74 | -0.29 | YES |
| 20 | 23 | -0.86 | -0.82 | 0.90 | 0.86 | YES |
| 21 | 24 | -0.86 | -0.63 | 0.24 | 0.15 | YES |
| 22 | 25 | -0.99 | -0.90 | 0.95 | 0.71 | YES |
| 23 | 26 | 0.16 | -0.50 | 0.94 | 0.63 | YES |
| 24 | 27 | -0.60 | 0.26 | 0.81 | -0.34 | YES |
| 25 | 28 | -0.86 | -0.49 | 0.90 | 0.83 | YES |
| 26 | 30 | -0.47 | -0.72 | 0.84 | 0.55 | YES |
| 27 | 32 | -0.91 | -0.76 | 0.21 | 0.37 | YES |
| 28 | 33 | -0.54 | -0.17 | 0.89 | -0.05 | YES |
| 29 | 34 | -0.95 | -0.15 | 0.55 | 0.51 | YES |
| 30 | 36 | 0.48 | 0.41 | 0.87 | -0.44 | YES |
| 31 | 37 | 0.19 | -0.27 | 0.16 | 0.19 | NO |
| 32 | 38 | -0.91 | -0.11 | 0.88 | 0.36 | YES |
| 33 | 39 | -0.93 | 0.25 | 0.87 | 0.19 | YES |
| 34 | 40 | -0.34 | -0.91 | 0.73 | 0.74 | YES |

* Strong Correlation is established by $|r| > 0.70$

FIG. 8

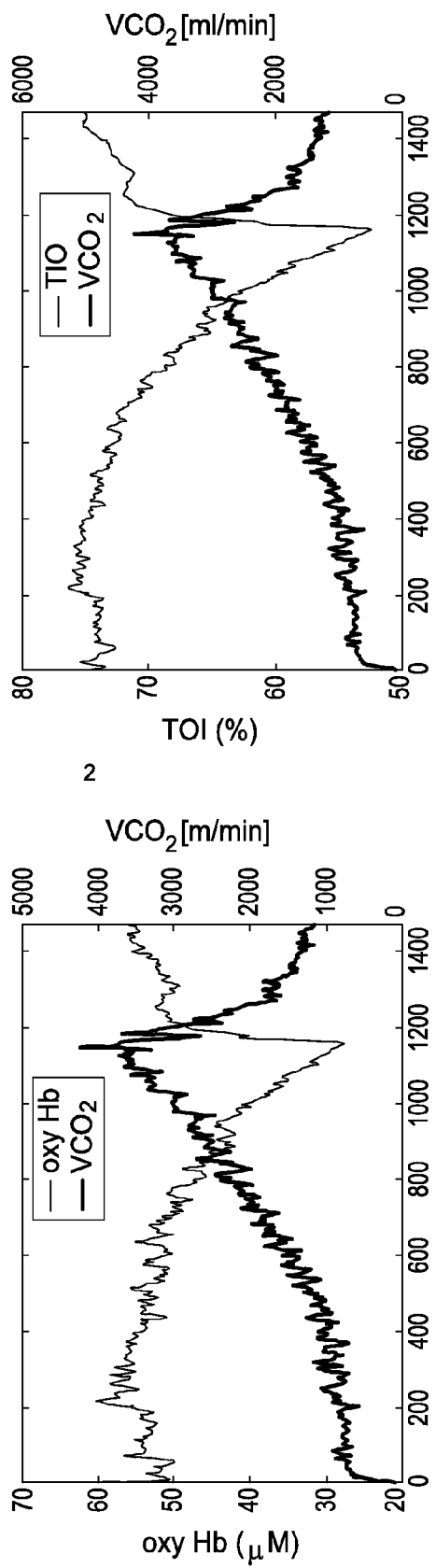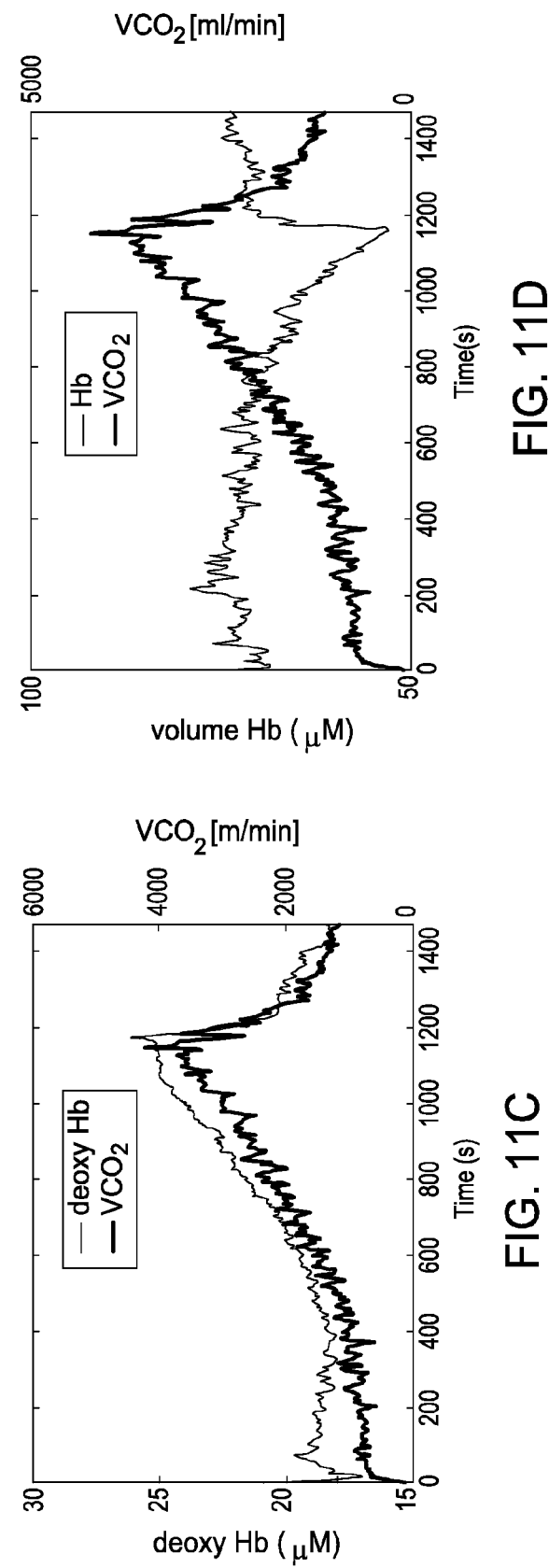
FIG. 11A
FIG. 11B
FIG. 11C
FIG. 11D

APPARATUS AND METHOD FOR IMPROVING TRAINING THRESHOLD

BACKGROUND OF THE INVENTION

1. Field of the Invention

Embodiments of the present invention generally relate to a non-invasive instrument to measure heart parameters and muscle parameters. More particularly, the invention relates to an apparatus and method for real-time assessment of a cardiac response to exercise and the ability of the peripheral muscle to utilize oxygen.

2. Description of the Related Art

Monitoring exertion via a heart rate monitor has long been a centerpiece of training for professional and performance athletes, as well as amateurs and retired players. However, physiologists and trainers agree that monitoring heart rate is a crude method and a lagging indicator of conditioning. Furthermore, mere measurement of heart rate fails to give a granular assessment of training threshold for highly conditioned athletes. Therefore, there is a need for a biosensor device for exercise monitoring.

SUMMARY OF THE INVENTION

The present invention generally relates to a non-invasive biosensor device configured to measure physiological parameters of a subject. In one aspect, a method of determining a training threshold of a subject is provided. The method includes the step of detecting an oxygenation parameter of a tissue of the subject using Near InfraRed Spectroscopy (NIRS). The method further includes the step of processing the oxygenation parameter. Additionally, the method includes the step of determining the training threshold of the subject using the result of the processing.

In another aspect, a biosensor device for determining a lactate threshold of a subject during exercise is provided. The biosensor device includes a housing and a detector disposed in the housing. The detector is configured to detect an oxygenation parameter of a tissue of the subject using Near InfraRed Spectroscopy (NIRS). The biosensor device further includes a processor configured to process the oxygenation parameter and determine the lactate threshold of the subject.

In a further aspect, a biosensor device for measuring parameters of a subject during exercise is provided. The biosensor includes a housing and a first detector disposed in the housing. The first detector is configured to measure oxygenation parameters of a muscle tissue of the subject. The biosensor further includes a second detector configured to measure photoplethysmography (PPT) of the subject. Additionally, the biosensor includes a third detector configured to measure electrocardiography (EKG) and derived systolic time intervals (STI) of the subject.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention, and are therefore not to be considered limiting of its scope, for the invention may admit to other equally effective embodiments.

FIGS. 4A and 4B illustrate plots of the correlation between the signal feature A and the concentration of lactate.

FIGS. 5A and 5B illustrate plots of the correlation between the signal feature B and the concentration of lactate.

FIG. 8 is a data table of the signal features A-D.

FIGS. 11A-11D illustrate plots of the physiological parameters measured by the device along side of alongside $VCO_2$.

DETAILED DESCRIPTION

The present invention generally relates to a non-invasive biosensor device configured to measure physiological parameters of a subject. The non-invasive biosensor device may be used by itself or in combination with other biosensor devices. The non-invasive biosensor device will be described herein in relation to lactate threshold, ventilatory threshold, and coronary artery disease (CAD). It is to be understood, however, that the non-invasive biosensor device may also be used in other applications, such as microcirculation analysis, cardiovascular diseases, newborn perfusion deficit, assessment of hemorrhage and shock, monitoring of fluid resuscitation, and cognitive studies, without departing from principles of the present invention.

Figure 1:
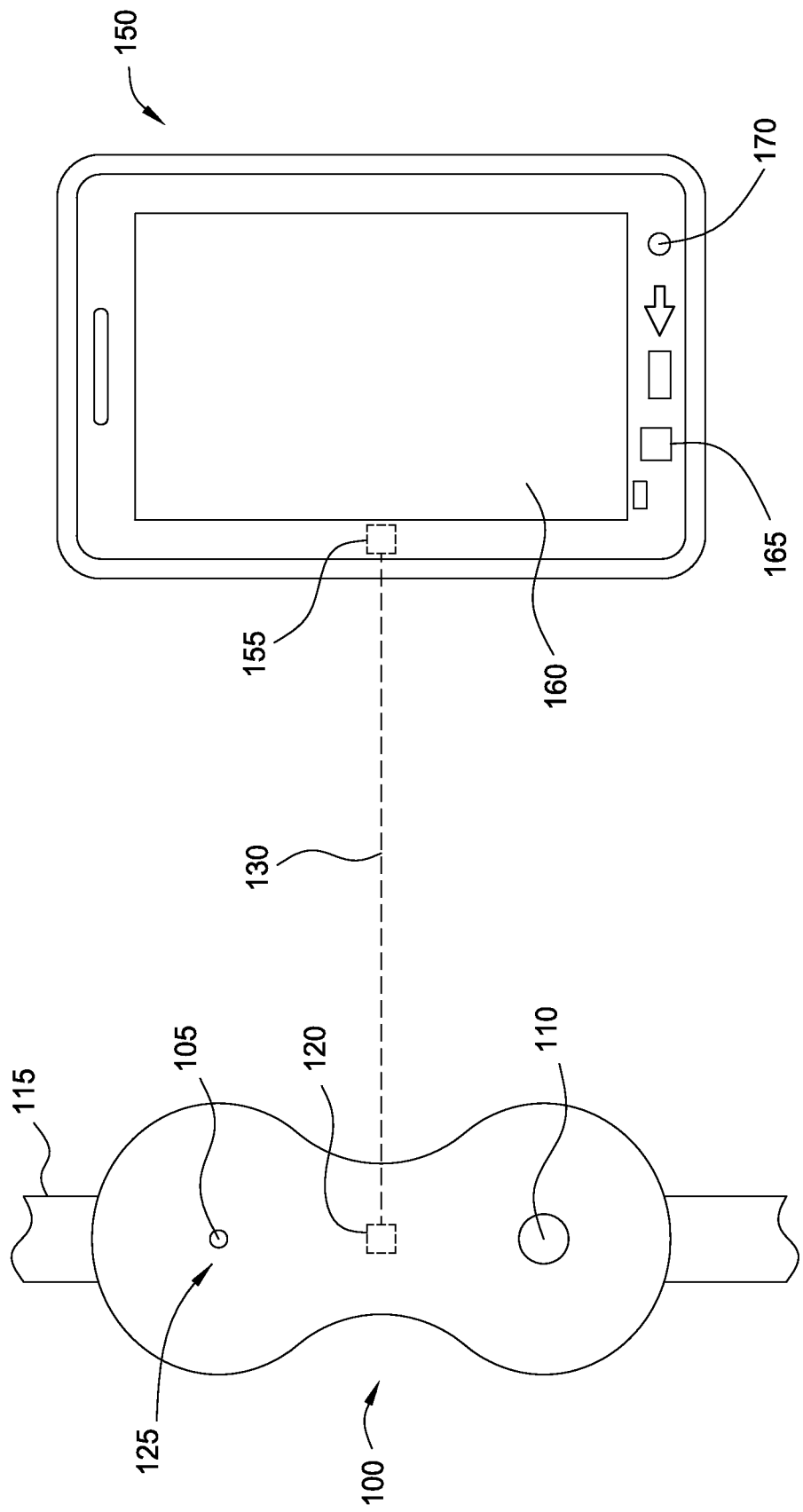
FIG. 1 illustrates a non-invasive biosensor device.

FIG. 1 illustrates a non-invasive biosensor device 100. The device 100 may be attached to a portion of the subject, such as a muscle mass via a strap 115. The device 100 will be described herein in relation to lactate threshold or ventilatory threshold. The device 100 may be used with an optional secondary device 150, such as a Smartphone (as shown), a watch, computer, mobile phone, tablet, a generic electronic processing and displaying unit, Cloud Storage, or a remote data repository via cellular network, or wireless Internet connection.

The device 100 includes a detector 125 that uses an optical technique called NIRS (Near InfraRed Spectroscopy). The detector 125 is configured to measure local muscle oxygenation parameters, such as oxy-hemoglobin [$HbO_2$] and deoxy-hemoglobin [HHb or HbR], and Tissue Oxygenation Index [TOI] non-invasively and in real time. The detector 125 includes an optical emitter 105 and an optical detector 110.

An example of a detector that uses is NIRS is described in WO 2009/050757 entitled METHOD AND INSTRUMENT FOR THE NON-INVASIVE MEASUREMENT OF THE OXYGEN/SATURATION OF BIOLOGICAL TISSUE, having an International Filing Date of 16 Oct. 2008, the entire contents of which are incorporated herein by reference. In general, the detector 125 uses two or more low-power lasers, LED or quasi-monochromatic light source and low-noise photodetecting electronics to measure the optical absorption of hemoglobin in oxygenated ($HbO_2$) and deoxygenated (HHb) states, water ($HbO_2$), and to calculate the molar concentration of such components in the muscle. In one embodiment, the detector 125 has a skin contact area of 3.5"×2". The device 100 may include a power supply, such as a battery, to supply power to the detector 125 and other components in the device 100. In another embodiment, the detector 125 can use a broad-spectrum optical source and a detector sensitive to the spectral components of light, such as a spectrometer, or a CCD or other linear photodetector coupled with near-infrared optical filters.

The detector 125 is an optoelectronic instrument, which, in association with a hardware part and relative piloting and data elaboration software is able to measure the characteristic optical absorption of a material at certain wavelengths belonging to the near infrared spectrum (NIR). From these measurements and elaboration of the data collected, an absolute level of the oxygenated hemoglobin concentration ($HbO_2$) and reduced hemoglobin (HHb), can be obtained that enables the oxygenation/saturation of a tissue to be established and displayed in real time. The detector 125 includes the optical emitter 105, which is an optical source that generates radiation NIR at a continual intensity. The optical source is made up of a preset number of independent modules, such as three or more, whose function is to generate a light radiation with wavelength in the NIR spectral range. The detector 125 includes the optical detector 110 that converts the light coming from the tissue into an electric signal and amplifies the signal. The detector 125 also includes a control unit that manages the timing of the system, the analog to digital conversion of the measurement signals and that controls the communication with the secondary device 150.

In order for the detector 125 to be able to obtain the absolute concentrations of hemoglobin with a continuous wave instrument, a method is implemented based on the water absorption peak method, using the optical absorption of water at a set wavelength, for example about 980 nm, as a reference to calculate the contribution of the scattering at the same wavelength. Water is the dominant absorbing chromofore at 980 nm; therefore, assuming that the optical absorption measured at 980 nm is totally due to water implies a reduced or negligible error. Since the concentration of water in muscles is fairly constant at 80% and the extinction coefficient of water at 980 nm is known, it is possible to calculate the scattering coefficient at 980 nm by solving the photon diffusion equation valid for highly scattering media such as human tissues. Given that the scattering coefficient is linearly related with the wavelength of the light, and that the coefficients of this relationship are known for many tissues, once the scattering coefficient at 980 nm has been measured, it can be calculated for the other wavelengths of the system. The light intensity that exits the tissue at a given geometric distance between the optical emitter 105 and the optical detector 110 is a function of the input optical intensity, of the distance between the optical emitter 105 and the optical detector 110, of the scattering coefficient and of the absorption coefficient. Once the spectrum of the scattering coefficient has been established, and the other variables being known, it is possible to calculate the absorption coefficient at the other wavelengths. To implement this processing method it is necessary to illuminate the tissue with at least three wavelengths, at least one of which must coincide with a water absorption peak, preferably at 980 nm. Thus, the optical source includes at least three luminous radiation emitter modules of different wavelengths. The optical emitter 105 and the optical detector 110 are placed directly in contact with the tissue to be examined. The optical emitter 105 delivers the light to the tissue, and the optical detector 110 collects the optically attenuated signal back-scattered from the tissue.

A single measuring cycle of the detector 125 consists in the sequential switching on of the optical emitter 105 that generates the light for a period of time T. During this period of time T, the tissue is stimulated by a radiation characterized by a set of wavelength λ and by a constant intensity $I_i(A)$; at the same time, the light exiting from the tissue, which has a mitigated intensity $I_o(\lambda)$, is measured by the optical detector 110. After time T, the optical emitter 105 is switched off and the optical detector 110 integrates for the same time T the detected signal, with the aim of measuring the offset that had superimposed over the stimulation signal. Once the switching on of all the light sources has been completed the measuring cycle stops with a $T_{OFF}$ wait period during which the tissue is not stimulated and the data collected is processed. This data is then sent to the control unit that generates a graph to be displayed on the device 150, to supply the continuous progress of the state of oxygenation of the tissue being examined.

The method of using the detector 125 includes the step of placing the optical emitter 105 and the optical detector 110 in contact with the tissue to be analyzed, and starting the measuring cycle by using an appropriate signal. The method also includes the step of emitting luminous radiations from the optical emitter 105 at a given optical intensity and at least at three different wavelengths in the near infrared spectrum, where at least one is correspondent to a water absorption peak, in particular 980 nm, for a localized illumination of the tissue. The method further includes the step of self adjusting of the offset parameters and sensitivity of the detector 125 based on the absorption level of the tissue examined and the external light intensity. Further, the method includes the step of detecting the optical intensity of the luminous radiations backscattered from the tissue using the optical detector 110 at a set distance from the illuminated zone and transforming the backscattered radiation detected in low noise electric signal. The method further includes the step calculating the absolute concentrations of oxygenated and reduced hemoglobin, according to the photon diffusion equation using the absorption coefficients previously calculated, and the step of calculating the absolute concentration of total hemoglobin as a sum of the hemoglobin oxygen and reduced hemoglobin concentrations and the oxygenation index of the tissue as the ratio of the oxygenated hemoglobin concentration over the total hemoglobin concentration. Additionally, the method includes the step of displaying the data on the secondary device 150. The steps for collecting, processing, analyzing, and calculating information from the detector 125 can be implemented in computer programs using standard programming techniques. The program code is applied to data generated by the detector 125 to perform the functions described herein and generate output information NIRS variables (e.g., physiological parameters). Each such computer program can be stored on the processor in the detector 125 or machine readable storage medium (e.g., CD ROM or magnetic diskette) that when read by the processor or other computer machines can cause the processor in the detector 125 to perform the analysis and control functions described herein.

The device 100 may be connected to the secondary device 150 via a data transmission path 130. The device 100 includes a transmission and reception unit 120, and the secondary device 150 includes a transmission and reception unit 155. The transmission and reception units 13*a*, 13*b* communicate via the data transmission path 130, which may be a wireless technology such as infrared technology, Bluetooth or radio technology or the data transmission path 130 may be a wire. The data generated by the detector 125 may be processed by a processor, such as a computer processor, in the device 100, and the processed data may be communicated to the secondary device 150 via the data transmission path 130. The processed data may be shown on a display 160 of the secondary device 150. The displayed processed data may be manipulated by the subject using control buttons 165, 170 on the secondary device 150. In another embodiment, the data generated by the detector 125 may be sent to the secondary device 150 via the data transmission path 130, and then a processor, such as a computer processor, in the secondary device 150 may process the data. The processed data by the secondary device 150 may be shown on the display 160 and manipulated by using control buttons 165, 170. In further embodiment, a portion of the data generated by the detector 125 may be processed by the processor in the device 100 and the (partial) processed data may be communicated to the secondary device 150 via the data transmission path 130 for further processing by the processor in the secondary device 150. In a similar manner, the processed data may be shown on the display 160 and manipulated by using control buttons 165, 170 in the secondary device 150. In another embodiment, the device 100 may operate as a single unit, wherein the data generated by the detector 125 may be processed by the processor in the device 100, and the processed data may be communicated by a communication module (not shown) that sends a signal to the subject, such as an auditory signal, a visual signal, a vibratory signal, or combinations thereof, when a predetermined event occurs during the exercising cycle.

The device 100 is used for the study of muscle tissue oxygenation during exercise. The application of this technology is particularly relevant in endurance type sports, such as running, cycling, multisport competition, rowing, etc., but can also be successfully applied to events of other types and distances. The device 100 is configured to wirelessly measure real-time muscle parameters during physical exercise. The device 100 may be secured to a selected muscle group of the subject, such as the leg muscles of the vastus lateralis or gastrocnemius which are primary muscle groups of running and cycling. The detector 125 in the device 100 uses a near infrared light emitter and sensor pair to non-invasively quantify both the absolute concentration of oxygenated and deoxygenated hemoglobin as well as relative oxygenation saturation in the selected muscle group.

Figure 2:
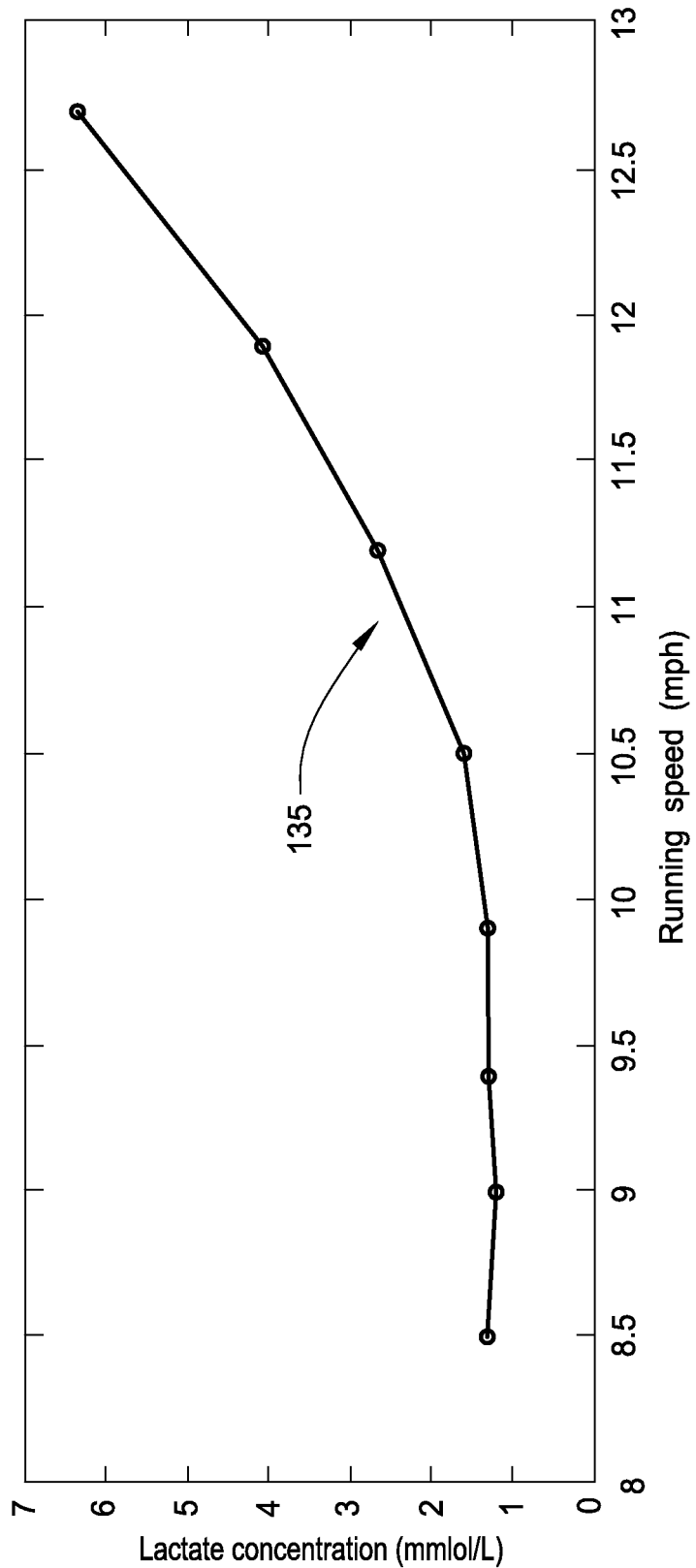
FIG. 2 illustrates a plot of a lactate curve.

Muscles increase their oxygen requirements during periods of increased stress (e.g. athletic activity). The more a muscle is being stressed the more oxygen is extracted from arterial blood to supply these needs. Therefore an appreciable desaturation of hemoglobin occurs in stressed muscles, which correlates with exercise intensity. At the same time, at rest and under steady-state exercise conditions, there is a balance between blood lactate production and its subsequent removal. As the muscles are stressed to greater and greater degrees more lactic acid is also produced as a byproduct. At a certain point (unique to each subject) the body begins producing more lactic acid than it can remove. FIG. 2 illustrates a plot of a lactate curve. The lactate threshold (LT) refers to the intensity of exercise at which there is an abrupt increase in blood lactate levels above baseline. The lactate threshold is shown in FIG. 2 as reference number 135. Coaches and trainers use the lactate threshold pace to generate training programs (frequently referred to as zone training) that are a combination of high volume low intensity, maximal steady-state, and supra-threshold interval workouts to improve athletic performance. Lactate threshold training is one way to improve athletic performance of the subject.

An exercise experiment was conducted with 40 subjects wearing the device 100 while exercising on a variable-speed treadmill. After warm-up, each subject was asked to choose a starting pace at which they could conduct a conversation with a running peer without fatigue. Then, the running pace was increased every 3 minutes by 20 seconds/mile (e.g., 8 min/mile, 7:40 min/mile, 7:20 min/mile, and so on). At the end of each running stage, the subject was asked to temporarily interrupt the run and to step aside of the treadmill to allow the examiner to take a capillary blood sample from the earlobe. The blood sample was chemically analyzed to provide the concentration of lactic acid or lactate (here indicated with [L]), accumulated in the bloodstream. After the subject reaches physical exhaustion, the subject was asked to walk on the treadmill for 5 minutes to recover. Out of the 40 subjects, 6 subjects were removed from the results due to equipment malfunction. Therefore, the following information on the exercise experiment will be based upon 34 subjects.

During the running protocol in the exercise experiment, the device 100 measured the following physiological parameters of the exercising muscle.

1. Concentration of oxygenated hemoglobin $[HbO_2]$;
2. Concentration of deoxygenated hemoglobin [HHb];
3. Total concentration of hemoglobin [tHb]

$$[tHb]=[HbO_2]+[HHb]$$

4. Tissue Oxygenation Index (TOI)

$$TOI=[HbO_2]//[tHb] \text{ or } TOI\%=100*([HbO_2]//[tHb]).$$

Unlike the lactate analysis that is performed once at the end of each 3-min running stage, the NIRS measurements by the detector 125 in the device 100 were continuously collected every 20 milliseconds. Filtering algorithms can be applied to reduce short-term oscillations of the NIRS signals.

During running stages, muscular cells increased their oxygen consumption to create energy necessary to compensate muscle contraction, and subsequently frequent muscle contractions reduced blood flow supplied to the muscle through capillaries. As a result, $[HbO_2]$, [tHb] and TOI values decreased, while [HHb] increased. Furthermore, the rates at which these oxygenation variables change are distinct. Immediately after the start of the run, the oxygenation as measured by $[HbO_2]$, [tHb], and TOI drastically decreased for 20-30 seconds indicated by an increased rate of change of these variables; subsequently, the muscle metabolism tended towards an equilibrium that induced more stable levels of oxygenation indicated by a relatively decreased rate of change of these variables. The time profile resembled an exponential decay.

Figure 3A:
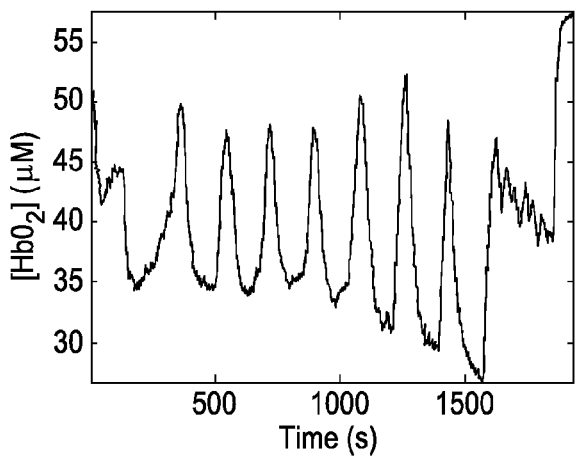
FIG. 3A illustrates a plot of the time course of the concentration of oxygenated hemoglobin [$HbO_2$].
Figure 3B:
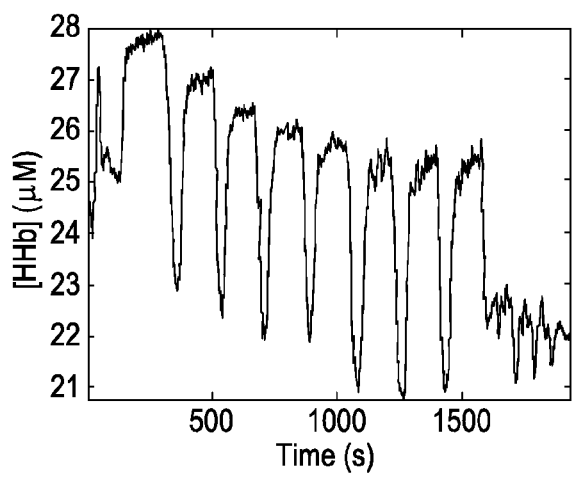
FIG. 3B illustrates a plot of the time course of the concentration of deoxygenated hemoglobin [HHb].
Figure 3C:
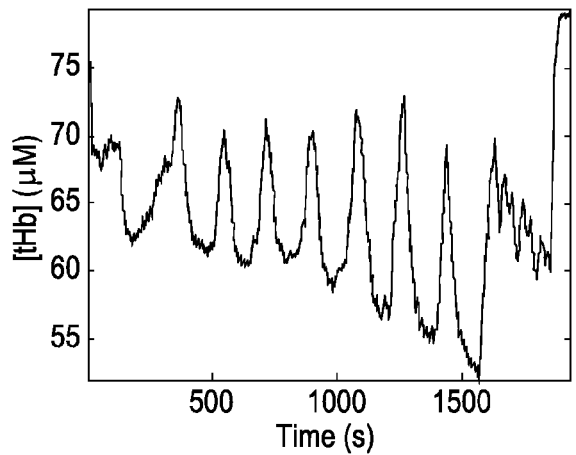
FIG. 3C illustrates a plot of the time course of the total concentration of hemoglobin [tHb].
Figure 3D:
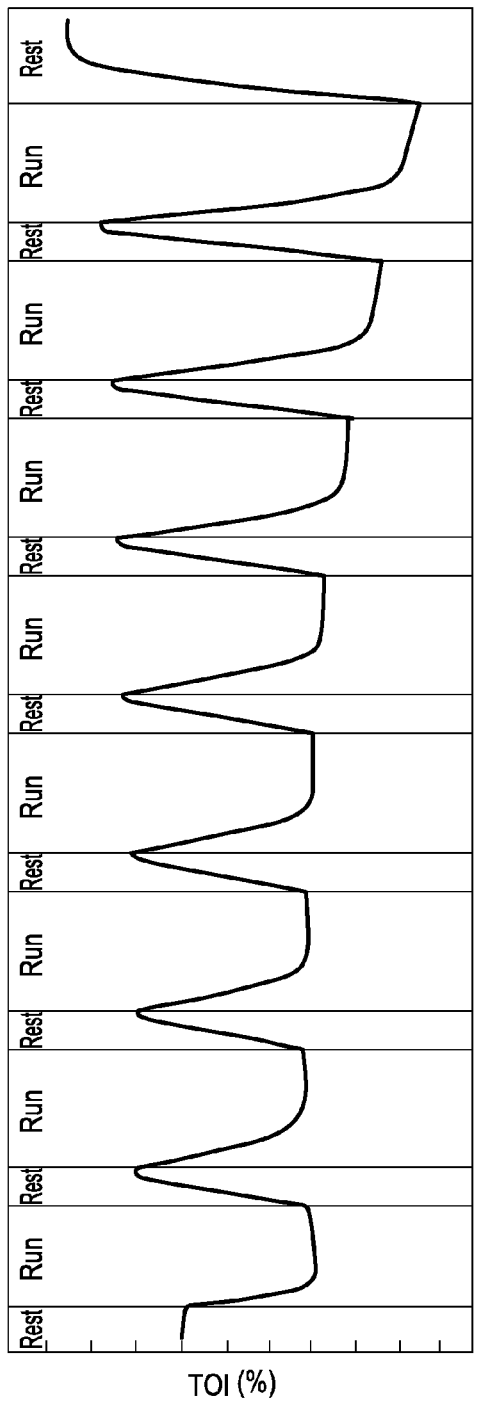
FIG. 3D illustrates a plot of the time course of the Tissue Oxygenation Index (TOI).

FIGS. 3A-3D illustrate plots of the physiological parameters measured by the device 100. FIG. 3A illustrates a plot of the time course of the concentration of oxygenated hemoglobin $[HbO_2]$. FIG. 3B illustrates a plot of the time course of the concentration of deoxygenated hemoglobin [HHb]. FIG. 3C illustrates a plot of the time course of the total concentration of hemoglobin [tHb]. FIG. 3D illustrates a plot of the time course of the Tissue Oxygenation Index (TOI). During periods of temporary rest due to blood sampling, the muscle inactivity caused reduced oxygen consumption and the lack of contraction allowed the supply of oxygen-rich blood. Consequently, [HbO$_2$], [tHb] and TOI increased rapidly, whereas [HHb] decreased. Furthermore, the rates at which these oxygenation variables change are distinct. Therefore, each running stage originated a specific signal change in each of the 4 NIRS variables associated with muscle desaturation, and each rest period favored the re-oxygenation of muscular tissues.

Although the signal profiles remained similar across running stages, some stage-to-stage changes were noticeable. To quantify such changes, 4 signal features were defined that aimed to describe the muscle oxygenation dynamics during running exercise. The signal features will be described in relation to the Tissue Oxygenation Index (TOI) as shown in FIG. 3D. However, the signal features may be described in relation to the other physiological parameters (e.g., [HbO$_2$], [HHb] and [tHb]) in a similar manner without departing from principles of the present invention.

Figure 3E:
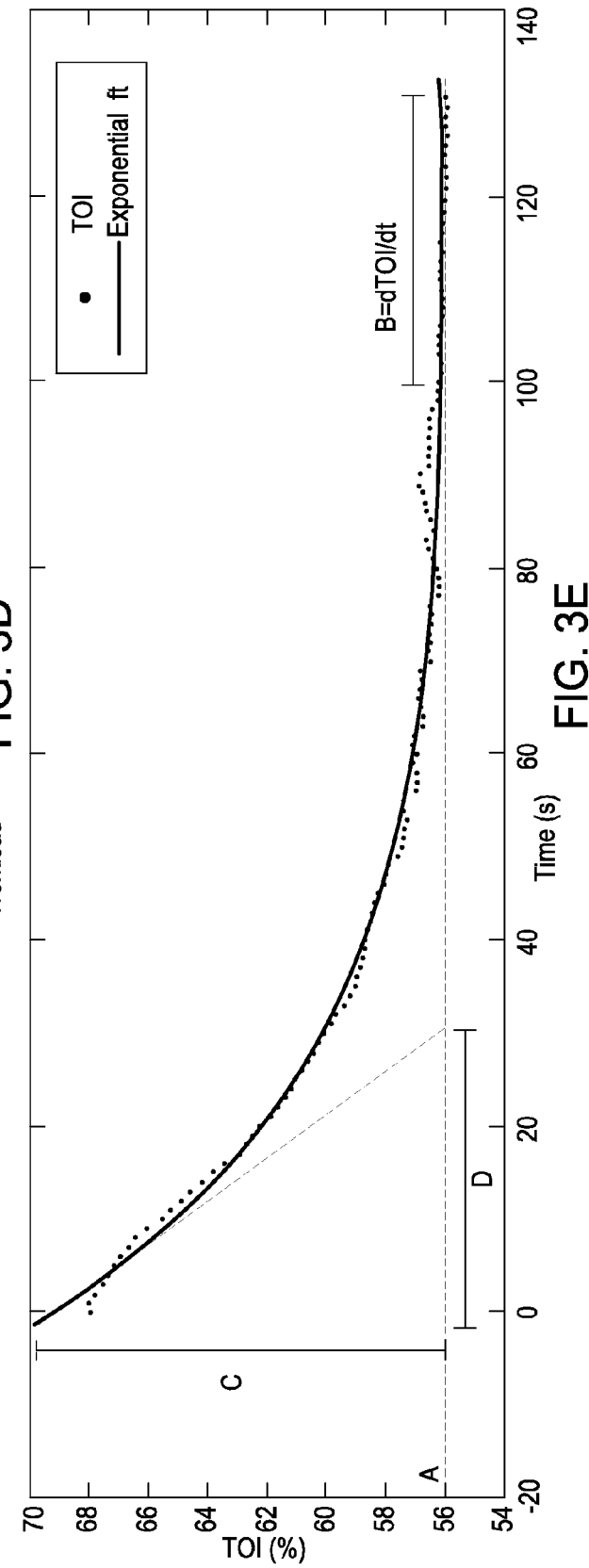
FIG. 3E illustrates a plot of a typical signal profile of TOI during a running stage shown in FIG. 3D.

FIG. 3E illustrates a plot of a typical signal profile of TOI during the running stage shown in FIG. 3D. The 4 signal features are shown in the plot in FIG. 3E as signal features A, B, C and D. The defined set of signal features describes the kinetic of the muscle oxygenation during each running stage. Although these features covers several aspects of the oxygenation kinetics (early rapid desaturation, late equilibrium), additional feature can be defined using different fitting models (polynomial, gaussian, rational, power, etc.) and related parameters can be extracted by those models.

The signal feature A is the value of TOI at the end of the running stage. Depending on the level of noise of the signal and the rate of change in the value of TOI, it is possible to use a single sample or an average of multiple samples selected from the plateaus of the TOI curve. The plateaus of the TOI curve are indicated by decreased rate of change in TOI values relative to the early rapid desaturation phase. Signal feature A indicates the balance between the availability of oxygenated blood and total blood at the end of the stage. As the workload of the exercise increases, the value of signal feature A decreases.

The signal feature B is based on the rate of change in the TOI which can be defined in this example by the slope of the linear model fit on the plateau interval of the TOI curve. During low-workload stages, the muscle contracts at a low frequency and the level of energy consumption is relatively low, therefore the muscle is able to slowly regain oxygenation at the plateau regime indicated by a positive rate of change in the TOI values. As the exercise becomes more intense in subsequent stages, the increased oxygen consumption causes the TOI plateau to shift towards stable oxygenation values during medium-intensity stages, and to decreasing values during high-intensity stages as indicated by a negative rate of change of TOI values. Therefore, the rate of change of TOI values, which, among other approaches, can be defined by the slope of the TOI plateau, provides information about the equilibrium of the oxygenation during incremental running protocols.

The signal feature C is based on the magnitude of the decay of the oxygenation variable which can be defined by the amplitude of the exponential model fit on the entire stage interval of the TOI curve. As exercise workload increases, the differential between the value of oxygenation at the beginning and the end of the running stage increases, due to increased contraction frequency and oxygen consumption.

The signal feature D is based on the decay rate of the oxygenation variable which can be defined by the time constant of the exponential model fit on the entire stage interval of the TOI curve. As exercise workload increases, the oxygen deprivation after the beginning of the run occurs quicker.

An unexpected result of the exercise experiment was the determination of linear relationships that existed between the defined signal features and the NIRS variables (e.g., physiological parameters), measured by the detector 125 in the device 100. For example, in the vast majority of the subjects, it was found that a negative correlation exists between the signal feature A and the concentration of lactate. FIG. 4A illustrates a plot of the signal feature A alongside the concentration of lactate in a selected subject, as a function of the running stage. In 19 out of 34 subjects (see table in FIG. 8), a linear relationship between signal feature A and the concentration of lactate had a correlation coefficient lower than −0.7 (−1 being the strongest negative correlation and +1 being the strongest positive correlation). FIG. 4B illustrates a plot of the correlation between the signal feature A and the lactate concentration.

In the exercise experiment, it was also determined that a negative correlation exists between the signal feature B and the concentration of lactate. FIG. 5A illustrates a plot of signal feature B alongside the concentration of lactate in a selected subject, as a function of the running stage. In 11 out of 34 subjects (see table in FIG. 8), a linear relationship between feature B and the concentration of lactate had a correlation coefficient lower than −0.7 (−1 being the strongest negative correlation and +1 being the strongest positive correlation). FIG. 5B illustrates a plot of the correlation between the signal feature B and the lactate concentration.

Figure 6A:
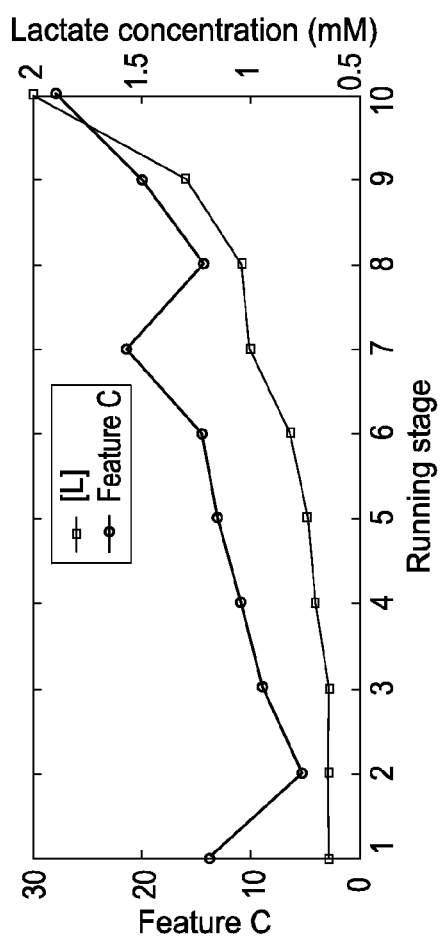
FIGS. 6A and 6B illustrate plots of the correlation between the signal feature C and the concentration of lactate.
Figure 6B:
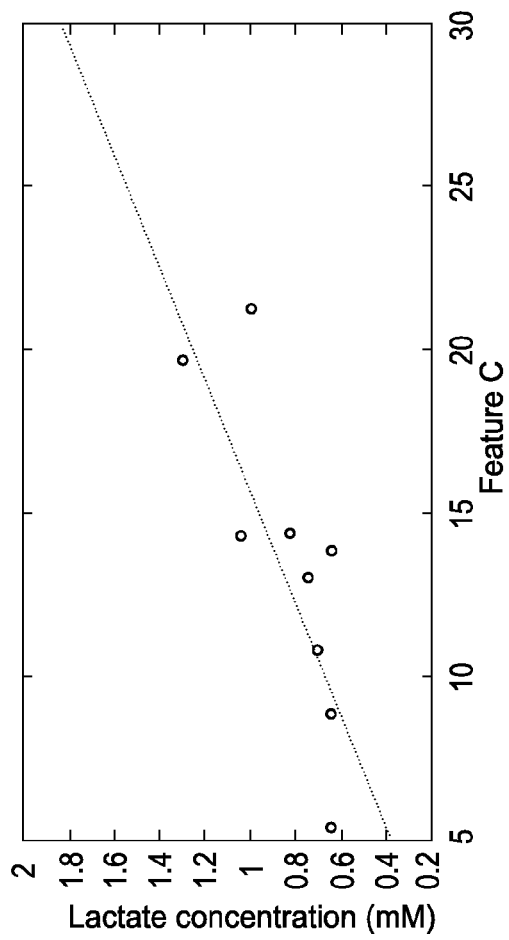

In the exercise experiment, it was further determined that a positive correlation exists between the signal feature C and the concentration of lactate. FIG. 6A illustrates a plot of the signal feature C alongside the concentration of lactate in a selected subject, as a function of running stage. In 25 out of 34 subjects (see table in FIG. 8), a linear relationship between signal feature C and the concentration of lactate had a correlation coefficient higher than 0.7 (−1 being the strongest negative correlation and +1 being the strongest positive correlation). FIG. 6B illustrates a plot of the correlation between the signal feature C and the lactate concentration.

Figure 7A:
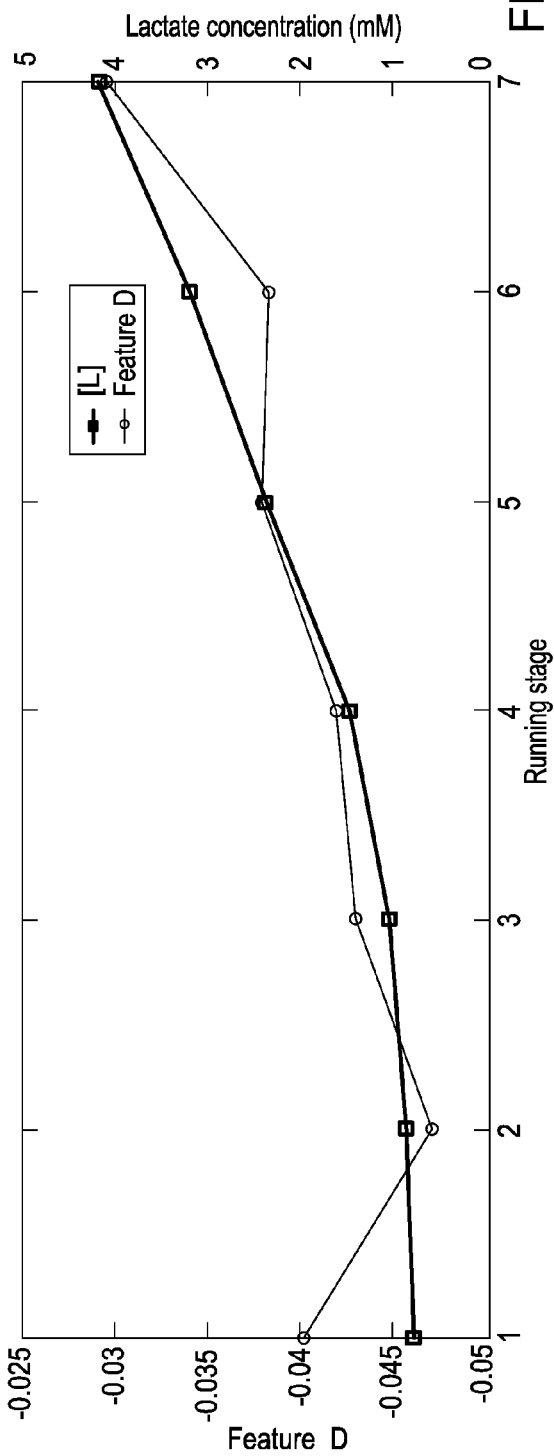
FIGS. 7A and 7B illustrate plots of the correlation between the signal feature D and the concentration of lactate.
Figure 7B:
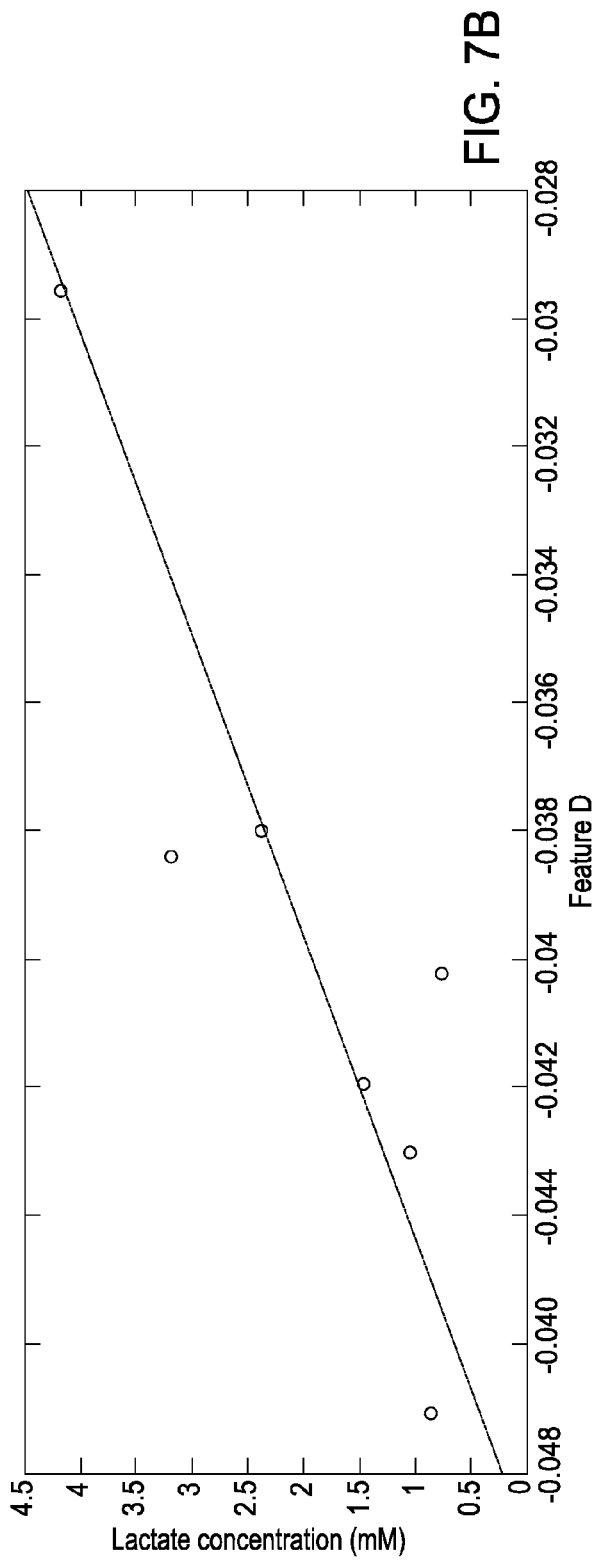

In addition, it was determined during the exercise equipment that a positive correlation exists between the signal feature D and the concentration of lactate. FIG. 7A illustrates a plot of the signal feature D alongside the concentration of lactate in a selected subject, as a function of the running stage. It was found that in 9 out of 34 subjects (see table in FIG. 8), a linear relationship between signal feature D and the concentration of lactate had a correlation coefficient higher than 0.7 (−1 being the strongest negative correlation and +1 being the strongest positive correlation). FIG. 7B illustrates a plot of the correlation between the signal feature D and the lactate concentration.

As set forth in FIGS. 4-7, a correlation exists for 32 out of 34 subjects in the exercise experiment between the one or more signal features A, B, C, D and the concentration of lactate. As a result, a curve profile as a function of the workload (speed or pace), equivalent of lactate can be derived for each subject. The curve profile for the subject would be similar to the curve profile shown in FIG. 2. Using the curve profile for the subject, an estimation of the lactate threshold can be performed. In exercise physiology, the lactate threshold (LT) is defined as the level of workload over which the mechanisms of lactate removal fail to keep pace with the lactate production. In a curve representing lactate concentration [L] as function of incremental workload, LT is identified as the workload at which the concentration of lactate abruptly increases compared to the baseline level. This methodology is widely reported in the exercise physiology literature. In the present invention, signal features A, B, C, D are used to derive a surrogate measure of lactate concentration on which the described method of LT determination can be applied. Features A, B, C, D are explanatory variables that can be used individually or combined to model the response variable [L]. In mathematical terms, the computed features allows the determination of the lactate concentration as:

$$[L]=f(A,B,C,D),$$

where f is a linear or non-linear function, [L] is the concentration of lactate and A,B,C,D are the signal features defined herein. In case of a multiple linear regression model, [L] is determined as:

$$[L]=a_1*A+a_2*B+a_3*C+a_4*D+\epsilon,$$

where $a_1$, $a_2$, $a_3$, $a_4$ are regressor coefficients and $\epsilon$ is an error term in the linear relationship between [L] and the explanatory variables A, B, C, and D.

Therefore it has been shown that the present device is capable of measuring the lactate curve of the subject in real time through the use of the device 100. One advantage of the device 100 is that lactate curve is not theoretical and does not depend in any way on subjective attributes of the subject or on other confounding variables. Rather, the lactate curve is objective and therefore the device 100 gives a real measurement of total athletic capacity of the subject, as well as relative level of momentary exertion compared to the total capacity.

The device 100 may also be used to estimate ventilatory threshold (VT) of the subject. An exercise experiment was conducted with subjects wearing the device 100 on their thigh (vastus lateralis muscle) while exercising on a stationary bicycle. The test began with the subject warming up at a resistance of 50 Watts for 5 minutes, cycling at a constant rate of 60 rpm. After the warm-up period, the resistance increased by 15 Watts each minute and the subject was asked to maintain the constant pedaling speed of 60 rpm. The exercise test continued until the subject reached exhaustion, or could no longer maintain the speed of 60 rpm.

During the biking protocol in the exercise experiment, the detector 125 in the device 100 measured the following physiological parameters of the exercising muscle.

1. Concentration of oxygenated hemoglobin [$HbO_2$];
2. Concentration of deoxygenated hemoglobin [HHb];
3. Total concentration of hemoglobin [tHb]

$$[tHb]=[HbO_2]+[HHb]$$

4. Tissue Oxygenation Index (TOI)

$$TOI=[HbO_2]//[tHb] \text{ or } TOI \% = 100*([HbO_2]//[tHb]).$$

The NIRS measurements by the detector 125 were continuously collected every 20 milliseconds. Filtering algorithms can be applied to reduce short-term oscillations of the NIRS signals. Simultaneously with the measurements collected from the detector 125, respiratory gas exchange via metabolic cart for oxygen uptake ($VO_2$), carbon dioxide ($VCO_2$) respiratory exchange ratio (RER), ventilatory equivalents of $O_2$ and $CO_2$, and ventilator threshold (VT) was analyzed.

During the bike exercise, muscular cells increased their oxygen consumption to create energy necessary to compensate muscle contraction, and subsequently frequent muscle contractions reduced blood flow supplied to the muscle. As a result, [$HbO_2$], [tHb] and TOI values decreased, while [HHb] increased. [$HbO_2$], [tHb] and TOI were found to be inversely correlated with $VO_2$ and $VCO_2$, whereas [HHb] was directly correlated.

Figure 9:
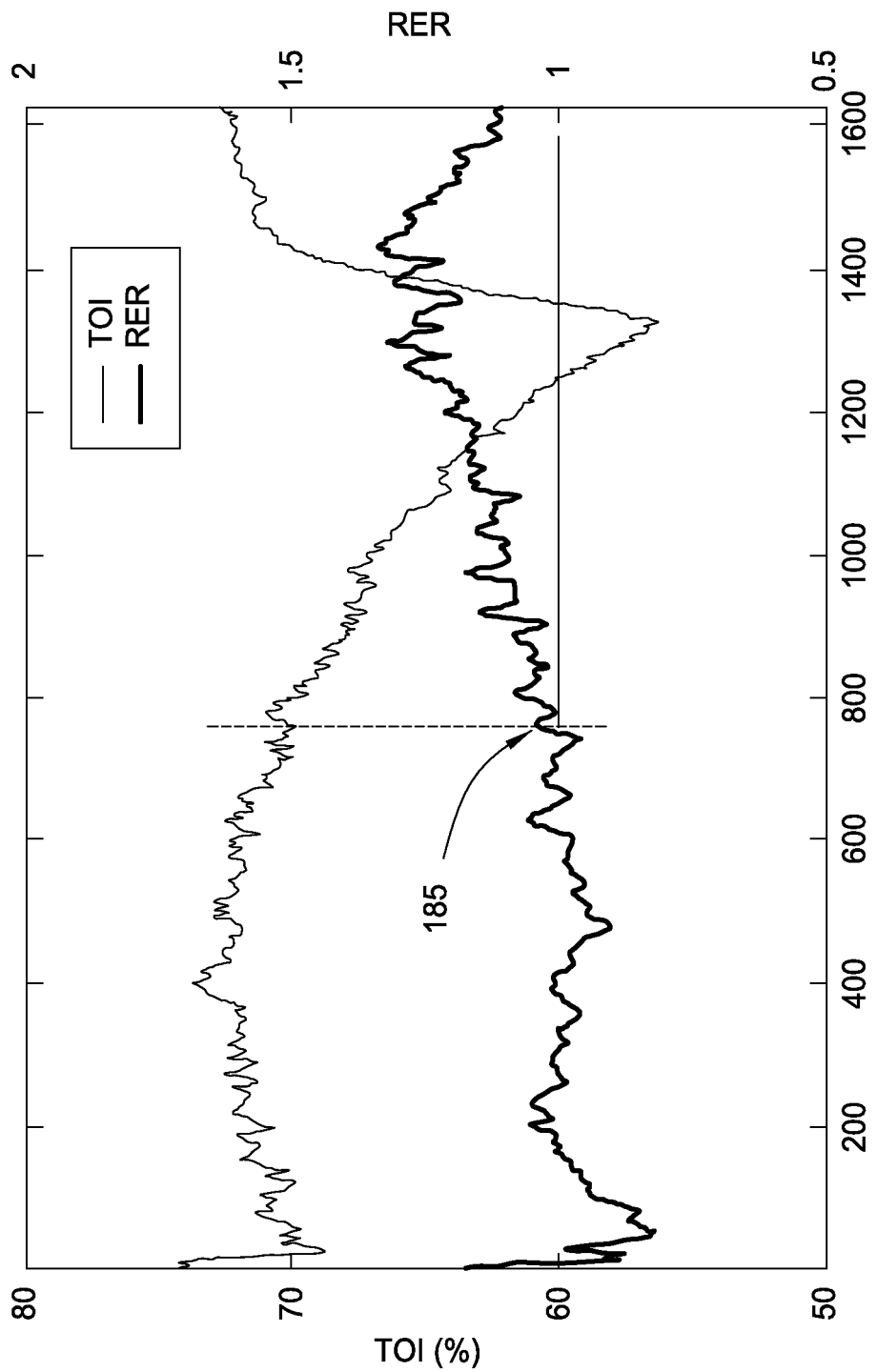
FIG. 9 illustrates a plot of a respiratory exchange ratio (RER) and TOI.

FIG. 9 illustrates a plot of a respiratory exchange ratio (RER) and TOI. Ventilatory threshold is determined from ventilatory changes that reflect a trend change in $CO_2$ extraction of the subject, $O_2$ consumption, and the breathing volume and rate. Ventilatory threshold is often correlated with the lactate threshold. Ventilatory threshold and lactate threshold indicate a trend toward accelerated or accumulating fatigue problems of the user. The muscle oxygen saturation (TOI) showed an initial steady state, followed by a linear decrease until physical exhaustion. The deflection point of the TOI trend coincides or slightly anticipates the ventilatory threshold (RER>1). Exercise physiologists define the ventilatory threshold as the level of workload over which the respiratory exchange ratio becomes stably greater that one. The ventilatory threshold is shown in FIG. 9 as reference number 185. Coaches and trainers use the ventilatory threshold pace to generate training programs (frequently referred to as zone training), that are a combination of high volume low intensity, maximal steady-state, and supra-threshold interval workouts to improve athletic performance. Ventilatory threshold training is one way to improve athletic performance of the subject.

Figure 10:
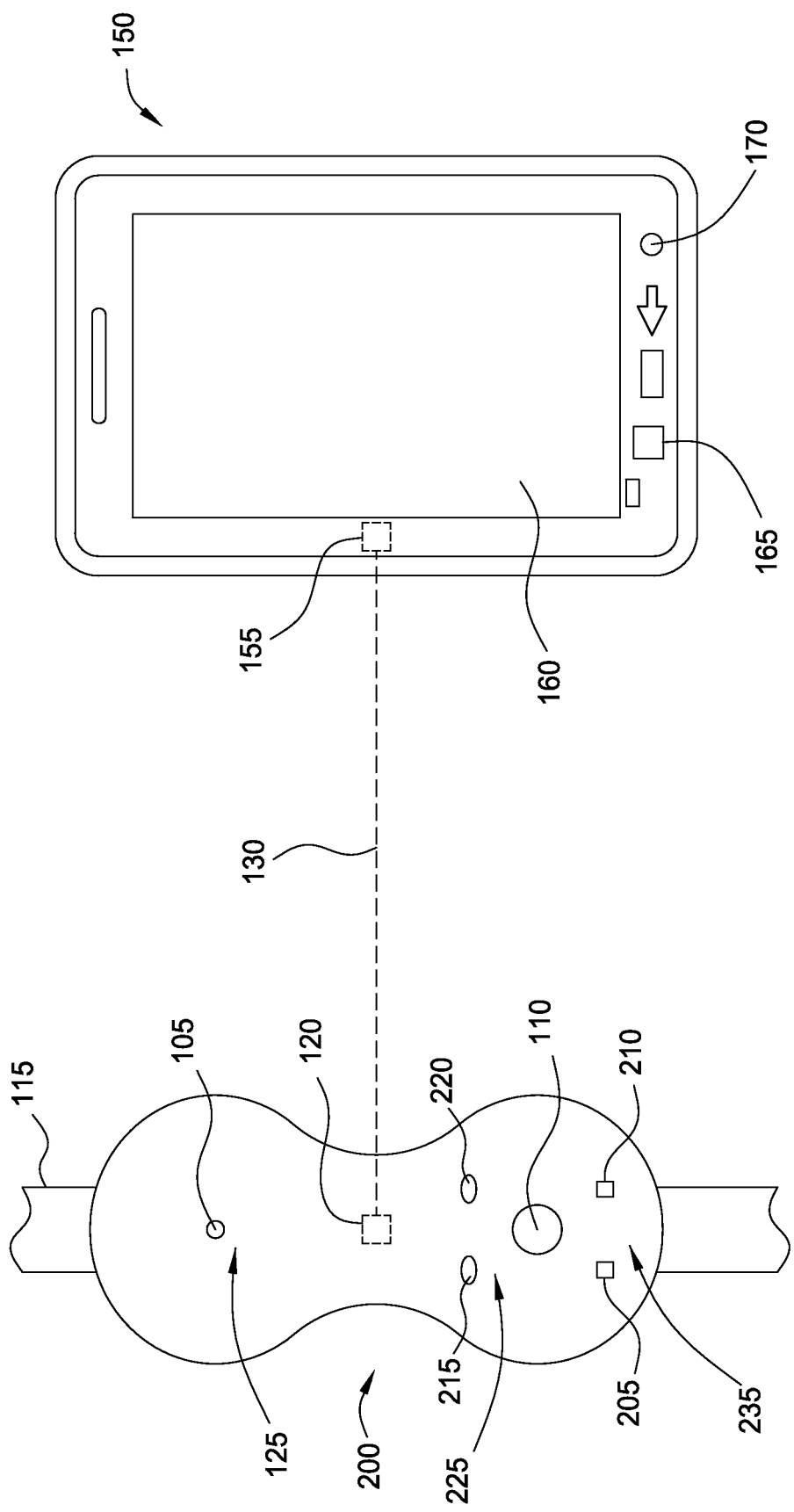
FIG. 10 illustrates a non-invasive biosensor device.

FIG. 10 is a view illustrating a non-invasive biosensor device 200. The components in the biosensor device 200 that are similar to the non-invasive biosensor device 100 will be labeled with the reference number. As shown, the device 200 includes the detector 125 which uses the optical technique called NIRS. The detector 125 is configured to measure local muscle oxygenation parameters, such as oxy-hemoglobin [$HbO_2$] and deoxy-hemoglobin [HHb or HbR], and Tissue Oxygenation Index [TOI] non-invasively and in real time. The detector 125 includes the optical emitter 105 and the optical detector 110.

The device 200 further includes a second detector 225 that is configured to measure photoplethysmography (PPT). The second detector 225 includes an optical emitter 215 and an optical detector 220. The device 200 also includes a third detector 235 that is configured to measure electrocardiography (EKG). The third detector 235 includes a first electrode 205 and a second electrode 210. The detectors 125, 225, 235 in the device 200 can measure NIRS parameters, electrocardiography, photoplethysmography, and derived systolic time intervals (STI) of the subject. The biosensor device 200 also includes a processor that is configured to analyze data generated by the detectors 125, 225, 235 to determine a cardiac response to exercise and the supply, arteriovenous difference, utilization of oxygen by the muscle tissue and hydration of the muscular tissue. The device 200 may include a power supply, such as a battery, to supply power to the detectors 125, 225, 235, and other components in the device 200.

The biosensor device 200 provides real-time assessment of the cardiac response to exercise and the ability of the peripheral muscle to utilize oxygen. By coupling a peripheral muscle assessment, using the detector 125 with a systemic cardiac assessment, using the detectors 225, 235, a complete picture of the effect of exercise and performance thresholds can be calculated and presented to both the subject and a monitor, such as a trainer or coach in real time.

The detector 125 is used to measure the levels of oxygenated and deoxygenated hemoglobin, the total volume of hemoglobin, and the tissue saturation index measured as a quotient between oxygenated and total hemoglobin, as well as the degree of hydration in muscle, while the muscle is working. These parameters, alone or combined together, provide a measurement or oxygen supply to the muscle, arteriovenous difference, and oxygen consumption of the muscle. Simultaneously, the detectors 225, 235 measure the electrical activity of the heart and the amplitude of the blood wave at the periphery, such as at a limb. The relationship is used between the electrical measure of the heart and its resulting pulse to infer a specific feature of the cardiac output (i.e., the ability of the heart to eject blood). As a byproduct, the device 200 is able to measure heart rate as well. In using the data from the detector 125 and the detectors 225, 235, these muscular and cardiac measures are leading indicators of training thresholds, and accurately describe the interplay between cardiac performance and muscle activity. The device 200 is able to trace the effects of training and to warn off over-exertion prior to it becoming evident to the subject.

The device 200 is configured to measure electrocardiography (EKG), photoplethysmography (PPT), systolic time interval (STI), and local muscle oxygenation parameters (molar concentration of oxy-hemoglobin [$HbO_2$], deoxy-hemoglobin [HHb], total volume of hemoglobin [tHb], and Tissue Oxygenation Index [TOI]), non-invasively and in real time. The subject can wear the portable device 200 on his or her waist, and the data is wirelessly sent via the data transmission path 130 to secondary device 150. The data generated by the detectors 125, 225, 235 may be processed by a processor in the device 200, and the processed data may be communicated to the secondary device 150 via the data transmission path 130. The processed data may be shown on a display 160 of the secondary device 150. The displayed processed data may be manipulated using control buttons 165, 170 on the secondary device 150. In another embodiment, the data generated by the detectors 125, 225, 235 may be sent to the secondary device 150 via the data transmission path 130, and then a processor in the secondary device 150 may process the data. The processed data by the secondary device 150 may be shown on the display 160 and manipulated by using control buttons 165, 170. In further embodiment, a portion of the data generated by the detectors 125, 225, 235 may be processed by the processor in the device 200 and the (partial) processed data may be communicated to the secondary device 150 via the data transmission path 130 for further processing by the processor in the secondary device 150. In a similar manner, the processed data may be shown on the display 160 and manipulated by using control buttons 165, 170 in the secondary device 150. In another embodiment, the device 200 may operate as a single unit, wherein the data generated by the detectors 125, 225, 235 may be processed by the processor in the device 200, and the processed data may be communicated by a communication module (not shown) that sends a signal to the subject, such as an auditory signal, a visual signal, a vibratory signal, or combinations thereof, when a predetermined event occurs during the exercising cycle.

The device 200, shown in FIG. 11, includes detectors 125, 225, 235 integrated into a single unit. In another embodiment, the detector 125 that measures NIRS parameters may be a separate device (similar to device 100), the detector 225 that measures photoplethysmography (PPT) may be separate device, such as a finger clip photoplethysmography, and the detector 235 that measures EKG may be separate device, such as a EKG leads or chest strap, or combinations thereof. Additionally, the detector 125 (i.e., NIRS probe), may be further miniaturized, and multiple probes will be used to enable simultaneous readings on different groups of muscles.

An exercise experiment was conducted with subjects wearing the biosensor device 200 while exercising on a stationary bicycle. The test began with the subject warming up at a resistance of 50 Watts for 5 minutes, cycling at a constant rate of 60 rpm. After the warm-up period, the resistance increased by 15 Watts each minute and the subject was asked to maintain the constant speed of 60 rpm. The exercise test continued until the subject reached exhaustion, or could no longer maintain the speed of 60 rpm. The test concluded with 5 minutes of recovery at the initial resistance of 50 Watts. Simultaneously with the measurements collected from the biosensor device 200, respiratory gas exchange via metabolic cart for oxygen uptake ($VO_2$) respiratory exchange ratio (RER), ventilator equivalents of $O_2$ and $CO_2$, and ventilator threshold (VT) was analyzed.

FIGS. 11A-11D illustrate plots of the physiological parameters measured by the device 200 along side of alongside $VCO_2$. FIG. 11A illustrates a plot of the time course of the concentration of oxygenated hemoglobin [$HbO_2$] alongside $VCO_2$. FIG. 11B illustrates a plot of the time course of the Tissue Oxygenation Index (TOI) alongside $VCO_2$. FIG. 11C illustrates a plot of the time course of the concentration of deoxygenated hemoglobin [HHb] alongside $VCO_2$. FIG. 11D illustrates a plot of the time course of the total concentration of hemoglobin [tHb] alongside $VCO_2$. The concentration of deoxy-hemoglobin [HHb] closely tracks the systemic oxygen intake ($r>0.92$, $p<0.0001$) across all subjects. The muscle oxygen saturation (TOI) showed an initial steady state, followed by a linear decrease until physical exhaustion. The deflection point of the TOI trend coincides or slightly anticipates the ventilatory threshold (RER>1) as shown in the graph in FIG. 9. It was determined that repeated measures of local oxygenation are highly consistent within subjects, but exhibit some differences amongst different subjects. It appears that local oxygenation measures are related to peripheral adaptation to exercise.

Unlike heart rate monitors, the biosensor device 200 gives subjects relevant, personalized information about their whole body's fitness status in real-time when there is time to adjust their ongoing workout and optimize their exercise to meet their training goals. To achieve this, measurements by the detectors 225, 235 of electrocardiogram and derived parameters (including but not limited to heart rate, time interval between R waves, variability or R-R interval), photoplethysmography and derived parameters (time interval between consecutive peaks, troughs, points of maximum and minimum slopes and higher order derivatives), systolic time intervals, and derived parameters (time interval between the ECG R-wave and the peak, trough, point of maximum slope and minimum or maximum of higher order derivatives of the photoplethysmography waves), and the detector 125 measures (concentration of oxygenated and deoxygenated hemoglobin, total volume of hemoglobin, oxygenation index as quotient of oxygenated, and total concentration of hemoglobin, derived arteriovenous difference, and blood flow) will be combined using analytical methods including, but not limited to, linear and non-linear correlations, component analysis, waveform feature extraction (peaks, troughs, inflection and deflection points, zero-crossing), Bayesian statistics, classification and clustering.

The biosensor device 200 may be used for cardiac rehabilitation. Coronary artery disease (CAD) has become more of a chronic disease in recent years as a result of effective treatment of acute ischemia. Chronic CAD is characterized by a variety of symptoms including pain, breathlessness, and fatigue. In chronic CAD, exercise capacity and maximum oxygen intake ($VO_2max$) are substantially reduced, compared to the normal population. Structured cardiac rehabilitation is the standard of care following a cardiac event or surgery. However, there is disagreement as to appropriate standards, thresholds, and end points of the exercise prescription. Finally, there is consensus that cardiac rehabilitation needs to be carried into the home and made a part of the patient's day-to-day routine, however, reliable and reproducible methods of ensuring this do not exist.

Exercise activity induces an increase in left ventricular wall thickness and volume as well as augmented myocardial contractility in healthy subjects. In cardiac patients, a consensus indicates that peripheral adaptation to exercise develops faster than cardiac adaptation. Conventional measures of exercise fail to differentiate cardiac from peripheral adaptation, but both are important in exercise assessment. More granularity such as measuring stroke volume and arterio-venous content difference would require invasive procedures that are not adaptable to longitudinal and home use. Therefore, the design, development, and validation of a wearable device capable of quantifying cardiac and peripheral adaptation to exercise non-invasively are a highly worthwhile effort. Such an intervention allows a more profound understanding of how the oxygen transport and metabolic processes progress during the rehabilitation period and can be coupled with an individualized, evidence-based exercise prescription. This prescription could be executed in the institutional setting and then translated to the outpatient arena.

The biosensor device 200 described herein introduces a new paradigm of exercise monitoring that is valid for both healthy and CAD populations. Monitoring the oxygen metabolism of the skeletal muscles provides real-time, accurate information on physical exertion, and that information, paired with systemic parameters, yields a complete description of individual exercise performance. The biosensor device 200 uses near-infrared spectroscopy (NIRS) to investigate the muscular oxygen supply and consumption, and electrocardiography and photo-plethysmography to measure the systemic response to exercise in real-time. These techniques are entirely non-invasive. The biosensor device 200 may be wirelessly connected to a local gateway that transmits the data remotely for cloud computing and storage.

An exercise experiment was conducted to determine the statistical correlation between the physiological parameters measured with the biosensor device 200 ([Hb02], [HHb], [tHb], [TOI], HR, systolic time interval STI) and ventilatory exchange readings (V02, VC02, VE/02, VE/C02, VT) performed with a metabolic cart. The oxygen metabolism of the right vastus lateralis muscle using anatomic landmarks was reviewed to ensure placement consistency across subjects. The results show that the concentration of deoxy-hemoglobin [Hhb] closely tracks the systemic oxygen intake (r>0.92, p<0.0001). It was found that repeated measures of local oxygenation are highly consistent within subjects, but exhibit some differences amongst different subjects. The local oxygenation measures are related to peripheral adaptation to exercise. For instance, it was observed that a local oxygen desaturation phase begins in correspondence with, or prior to, the transition to the anaerobic phase of the exercise, estimated when the respiratory exchange ratio becomes greater than one.

The biosensor device 200 described herein is a portable system that will seamlessly collect physiological information in real-time, and will infer an individualized measure of the oxygen capacity to be used as an indication of the effectiveness of cardiac rehabilitation programs. At the same time, the biosensor device 200 may be used as a development platform that exploits existent communication infrastructures, and integrates with other telemonitoring systems. The biosensor device 200 can be used in telemedicine and individualized medicine arenas. Furthermore, the use of the biosensor device 200 will facilitate future involvement in sports and physical fitness that will particularly benefit low-income population.

The biosensor device 200 has been developed to introduce a new paradigm of exercise monitoring. The monitoring of the oxygen metabolism of the skeletal muscles provides real-time, accurate information on physical exertion, and that information, paired with systemic parameters, yields a complete description of individual exercise performance. As discussed herein, near-infrared spectroscopy (NIRS) is used to investigate the muscular oxygen saturation, electrocardiography and photo-plethysmography to measure the systemic response to exercise in real-time. These techniques are entirely non-invasive. The system is wirelessly connected to a local gateway that transmits the data remotely for cloud computing and storage. The device 200 is a portable system that will seamlessly collect physiological information in real-time. The biosensor device 200 will provide athletes with moment-to-moment indicators of their exercise, thus allowing more accurate training and extension of the performance threshold.

An exercise experiment was conducted with subjects wearing the biosensor device 200 while exercising on a stationary bicycle. The volunteers performed a cycling exercise protocol consisting of 5 minutes of warm-up at a constant workload of 50 W, followed by a graded increment of 15 W/min until volitional exhaustion, while maintaining a pedaling cadence of 60±3 rpm throughout the experiment. The termination of the exercise was determined by the inability of the subject to maintain the imposed cadence. The exercise equipment consisted of a stationary road bike linked to an electronic load generator calibrated to the weight of each subject before the experiment. Respiratory gases were collected and analyzed using a breath-to-breath metabolic cart, which provides measurements of oxygen uptake, stroke volume and cardiac output. The workload was normalized to perform a group analysis independent of the maximal workload elicited by the subjects; all variables were samples at 10% workload intervals, where 0% is intended as the baseline workload at 50 W.

Figure 12B:
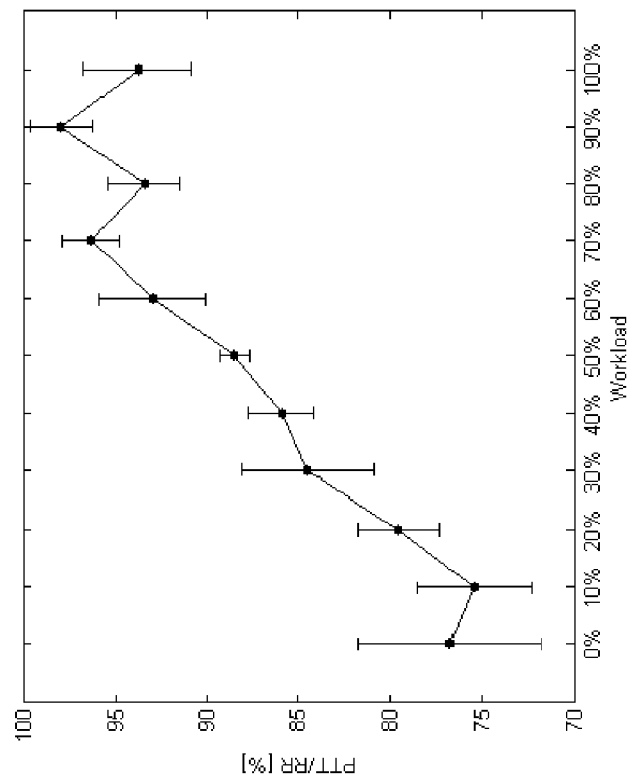
FIG. 12B is a plot of Percent ratio between pulse transit time (PTT) and R-R interval.
Figure 12A:
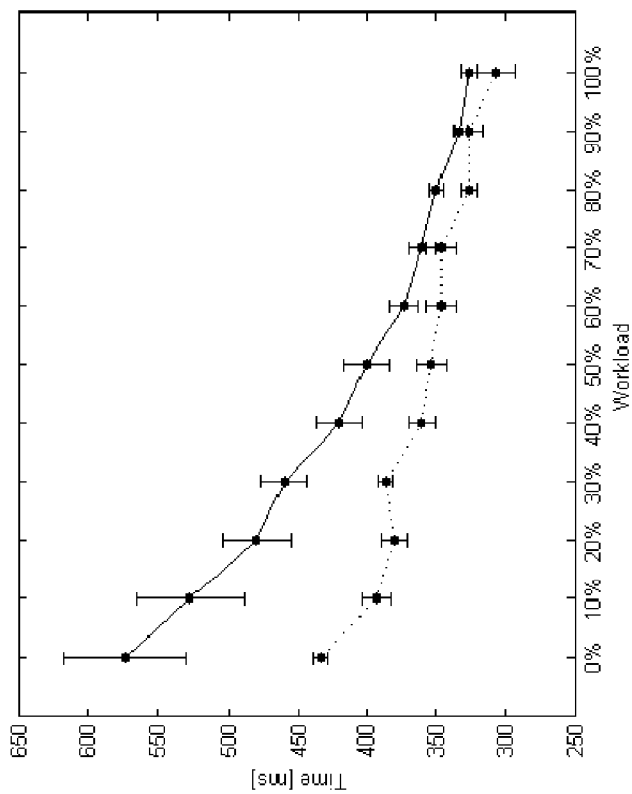
FIG. 12A is a plot of R-R interval and pulse transit time as a function of normalized workload.

FIG. 12A is a plot of R-R interval and pulse transit time as a function of normalized workload. The R-R interval is illustrated as a solid line and the pulse transit time is illustrated as a dashed line. As shown in FIG. 12A, both R-R interval and pulse transit time (PTT) of the subjects decreased throughout the duration of the exercise. The spread between R-R and PTT is as wide as 140 ms at the beginning of the exercise, but it gradually decreases until they assume similar values at maximum workload (300-320 ms). Heart rate (HR), calculated as the inverse of R-R interval, linearly increases ($R^2=0.98$) as a function of workload. The decreasing trend of PTT means a quicker delivery of arterial blood to the periphery, which indicates a progressive vasodilation of the major vessels. To further investigate the interplay between cardiac rate and vasodilation, the percent ratio between PTT and R-R interval was calculated. FIG. 12B is a plot of Percent ratio between pulse transit time (PTT) and R-R interval. The initial linear increase implies that the major contribution to augmented blood supply to the periphery comes from the increased heart rate; between 70% workload and exhaustion, the R-R interval increases at the same rate as the pulse transit time.

Figure 12D:
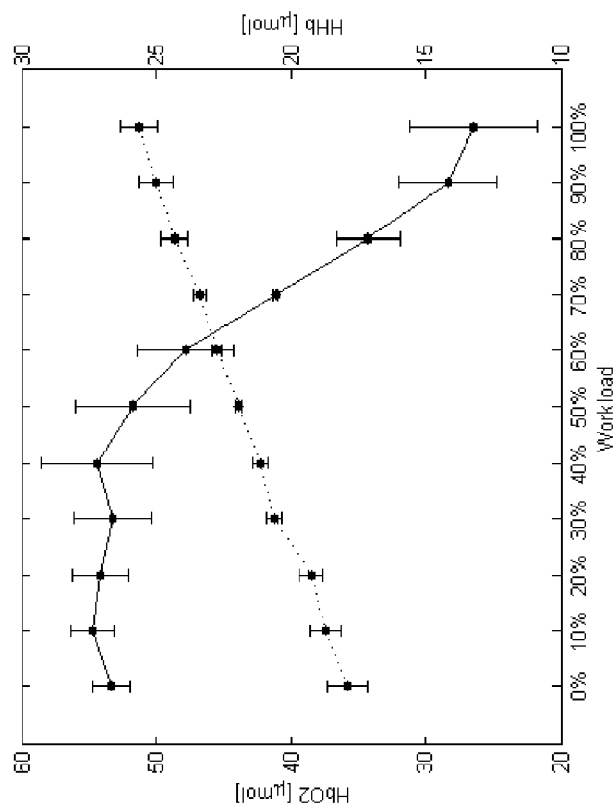
FIG. 12D is a plot of Oxyhemoglobin [$HbO_2$] and deoxyhemoglobin [HHb] as a function of normalized workload.
Figure 12C:
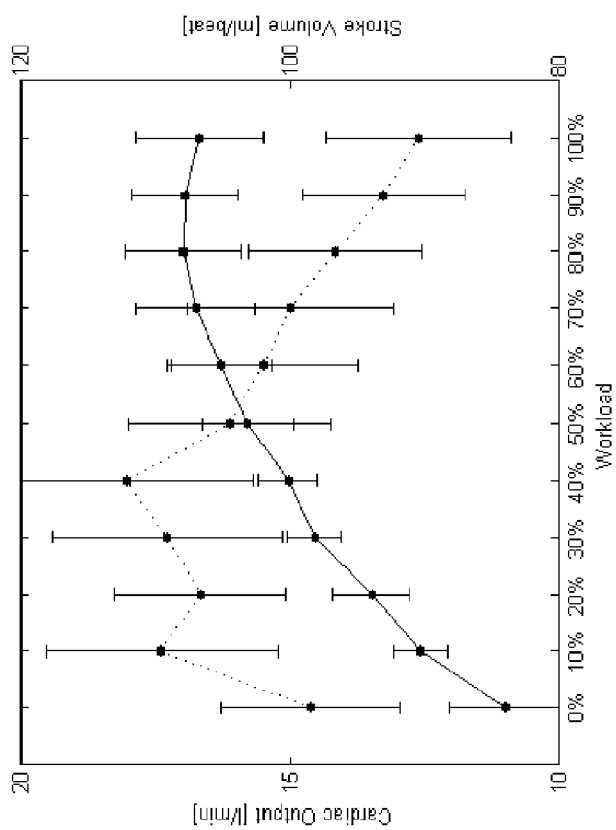
FIG. 12C is a plot of a cardiac output and stroke volume as function of normalized workload.

FIG. 12C is a plot of a cardiac output and stroke volume as function of normalized workload. The cardiac output (CO) is illustrated as a solid line and the stroke volume is illustrated as a dashed line. As shown, CO linearly increases during the phase of moderate exercise, followed by a moderate increase when the workload intensity becomes higher. The progressive diminution of stroke volume during vigorous exercise, in contrast with increased heart rate, is responsible for the final plateau of cardiac output (CO=HR·SV).

Figure 12E:
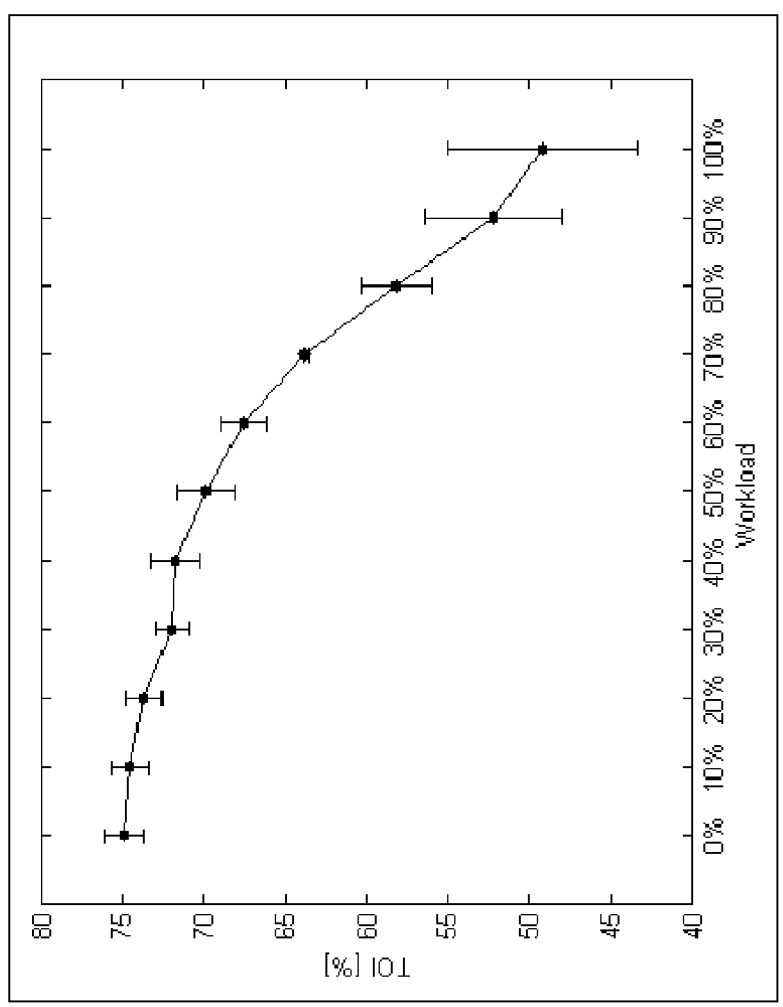
FIG. 12E is a plot of Tissue Oxygenation Index as function of normalized workload.

The molar concentration of $HbO_2$ remained constant during light and moderate exercise, and it abruptly decreased after 40% of normalized workload, with a maximum negative slope at 70% WL. The reduced standard error bars indicate a consistent desaturation pattern in all subjects, with a baseline value at 53.3±1.4 µM and desaturation range between baseline and exhaustion in the order of 30 µM. In turn, [HHb] showed a linear increase ($R^2=0.996$) throughout the exercise protocol, with the total excursion being 7.8 µM. FIG. 12D is a plot of Oxyhemoglobin [HbO$_2$] and deoxyhemoglobin [HHb] as a function of normalized workload. [HHb] closely tracks oxygen uptake and carbon dioxide trends ($R^2=0.96$, not reported here). Since the variation of [HbO$_2$] during maximal exercise was threefold, the correspondent change in [HHb] the total volume of hemoglobin [tHb] (not reported) followed a very similar decreasing trend of [HbO$_2$], with an average baseline-exhaustion difference of 23 µM. The muscle desaturation pattern described by tissue percent saturation index (TOI) is shown in FIG. 12E. Unlike [HbO$_2$], the TOI curve did not exhibit a well-defined deflection point at moderate workload. Instead, the muscle desaturation decay becomes more accentuated as the workload increases. All subjects showed consistent TOI values between 0% and 70% WL, whereas individual differences were noted during vigorous exercise. On average, the desaturation range from baseline to exhaustion was 25%. Since NIRS measures oxygenation mostly in the venous capillary compartment, the overall TOI drop indicates that about one-fourth of oxyhemoglobin in the venous return has been depleted of oxygen and utilized by muscular tissues.

The results show that the molar hemoglobin concentrations measured by NIRS were consistent amongst subjects. [HbO$_2$] exhibited a steady start followed by a steep desaturation from 40% workload onward, similar to what was observed for stroke volume. Deoxyhemoglobin [HHb] is strongly correlated to heart rate ($R^2=0.98$), oxygen uptake and carbon dioxide linear trends. The ratio between PTT and HR correlates with cardiac output ($R^2=0.90$); therefore, a combined measurement of ECG and PPG could potentially represent a novel method to assess cardiac output non-invasively. The relationship between CO and TOI is well modeled by a piece-wise linear trend with deflection at 40%-50% WL.

The results indicate that oxygen consumption at the skeletal muscle level initiates well before systemic variables, primarily cardiac output and RR/PTT, reach their plateau. The strong correlation between stroke volume and [HbO$_2$] also suggests that the stabilization of the cardiac pumping capacity after a moderate level of workload could be responsible for reduced oxygen supply to the periphery, and thus to the gradual transition from aerobic to anaerobic muscle metabolism. The exercise study shows that a combination of non-invasive methods such as NIRS, ECG and PPG delivers important information on the interplay between systemic and local muscular responses to exercise.

The present invention generally relates to a non-invasive biosensor device configured to measure physiological parameters of a subject. In one aspect, a method of determining a training threshold of a subject is provided. The method includes the step of detecting an oxygenation parameter of a tissue of the subject using Near InfraRed Spectroscopy (NIRS). The method further includes the step of processing the oxygenation parameter. Additionally, the method includes the step of determining the training threshold of the subject using the result of the processing.

In one or more embodiments, the training threshold is a lactate threshold of the subject.

In one or more embodiments, the training threshold is a ventilatory threshold of the subject.

In one or more embodiments, the oxygenation parameter comprises at least one of concentration of oxygenated hemoglobin, concentration of deoxygenated hemoglobin, total concentration of hemoglobin, and Tissue Oxygenation Index.

In one or more embodiments, processing the oxygenation parameter comprises analyzing a signal feature in a signal profile of the oxygenation parameter, the signal profile having a plurality of exercise stages.

In one or more embodiments, the signal feature is a value of the oxygenation parameter at an end of at least one of the plurality of exercise stages.

In one or more embodiments, the signal feature is a linear model fit on a plateau interval of a curve for at least one of the plurality of exercise stages.

In one or more embodiments, the signal feature is an amplitude of an exponential model of at least one of the plurality of exercise stages.

In one or more embodiments, the signal feature is a time constant of an exponential model of at least one of the plurality of exercise stages.

In one or more embodiments, the electrocardiography (EKG), photoplethysmography (PPT), and systolic time intervals (STI) of the subject is measured.

In one or more embodiments, measured data is analyzed to determine the cardiac response of the subject.

In one or more embodiments, detecting the oxygenation parameter comprises: delivering luminous radiations at a given optical intensity to a tissue of the subject; and detecting the optical intensity of the luminous radiations backscattered from the tissue.

In one or more embodiments, data is sent regarding the determined training threshold to a display of a secondary device.

In one or more embodiments, the subject is alerted when the subject has reached the training threshold.

In another aspect, a biosensor device for determining a lactate threshold of a subject during exercise is provided. The biosensor device includes a housing and a detector disposed in the housing. The detector is configured to detect an oxygenation parameter of a tissue of the subject using Near InfraRed Spectroscopy (NIRS). The biosensor device further includes a processor configured to process the oxygenation parameter and determine the lactate threshold of the subject.

In one or more embodiments, the processor is configured to analyze a signal feature in a signal profile of the oxygenation parameter, the signal profile having a plurality of exercise stages.

In a further aspect, a biosensor device for measuring parameters of a subject during exercise is provided. The biosensor includes a housing and a first detector disposed in the housing. The first detector is configured to measure oxygenation parameters of a muscle tissue of the subject. The biosensor further includes a second detector configured to measure photoplethysmography (PPT) of the subject. Additionally, the biosensor includes a third detector configured to measure electrocardiography (EKG) and derived systolic time intervals (STI) of the subject.

In one or more embodiments, a processor is configured to analyze data generated by the detectors to determine a cardiac response to exercise and utilization of oxygen by the muscle tissue.

In one or more embodiments, the second detector and the third detector are disposed in the housing.

In another aspect, a biosensor device for measuring parameters of a subject during exercise is provided. The device includes a first detector configured to measure electrocardiography (EKG), photoplethysmography (PPT), and derived systolic time intervals (STI) of the subject. The device further includes a second detector configured to measure oxygenation and hydration parameters of muscle tissue of the subject. Additionally, the device includes a processor configured to analyze data generated by the first detector and the second detector to determine a cardiac response to exercise and the supply, arteriovenous difference, utilization of oxygen by the muscle tissue and hydration of the muscular tissue.

In a further aspect, a method of determining a cardiac response to exercise and supply, arteriovenous difference and utilization of oxygen by a muscle tissue of a subject is provided. The method includes the step of measuring electrocardiography (EKG), photoplethysmography (PPT), and systolic time intervals (STI) of the subject. The method further includes the step of measuring oxygenation and hydration parameters of the muscle tissue of the subject. Additionally, the method includes the step of analyzing measured data to determine the cardiac response, and the utilization of oxygen by the muscle tissue.

While the foregoing is directed to embodiments of the present invention, other and further embodiments of the invention may be devised without departing from the basic scope thereof, and the scope thereof is determined by the claims that follow.

The invention claimed is:

1. A method comprising:
   emitting, at predetermined times, a radiation into a tissue of a subject;
   detecting, at corresponding predetermined times, a radiation emitted from the tissue of the subject;
   calculating, based on the detected radiation, an oxygenation parameter, at each of the corresponding times, of the tissue of the subject;
   processing, by one or more processors, the oxygenation parameter to generate one of a substantially real-time lactate curve or ventilatory curve, which is based on one or more signal features of the oxygenation parameter, wherein the oxygenation parameter comprises at least one of concentration of oxygenated hemoglobin, and concentration of deoxygenated hemoglobin, total concentration of hemoglobin, and Tissue Oxygenation Index;
   determining whether the lactate curve substantially contains a lactate threshold of the subject or the ventilatory curve substantially contains a ventilatory threshold of the subject; and
   providing an alert based on the determination that lactate curve substantially contains a lactate threshold or the ventilatory curve substantially contains a ventilatory threshold of the subject;
   wherein the one or more signal features comprises:
   a first signal feature comprising a oxygenation parameter value during an exercise stage;
   a second signal feature comprising a change in the oxygenation parameter value;
   a third signal feature comprising a rate of change in the oxygenation parameter value;
   a fourth signal feature comprising a scale of change in the oxygenation parameter value.

2. The method of claim 1, wherein processing the oxygenation parameter comprises analyzing the one or more signal features in a signal profile of the oxygenation parameter.

3. The method of claim 2, wherein the one or more signal features is a characteristic in the signal profile.

4. The method of claim 2, wherein the signal feature is a linear model fit on a plateau interval of a curve of the oxygenation parameter.

5. The method of claim 2, wherein the signal feature is an amplitude of an exponential model of the oxygenation parameter.

6. The method of claim 2, wherein the signal feature is a time constant of an exponential model of the oxygenation parameter.

7. The method of claim 1, further comprising measuring electrocardiography (EKG), photoplethysmography (PPT), and systolic time intervals (STI) of the subject.

8. The method of claim 7, further comprising analyzing measured data to determine the cardiac response of the subject.

9. The method of claim 1, wherein detecting the oxygenation parameter comprises:
   delivering luminous radiations at a given optical intensity to a tissue of the subject; and
   detecting the optical intensity of the luminous radiations backscattered from the tissue.

10. The method of claim 1, further comprising sending data regarding the lactate curve or ventilatory curve to a display of a secondary device.

11. The method of claim 1, further comprising alerting the subject when the subject has reached on or about the lactate threshold or the ventilatory threshold.

12. The method of claim 1, wherein the processing the oxygenation parameter generates the substantially real-time lactate curve based on four signal features, wherein the lactate curve provides real measurement of total athletic capacity of the subject and relative level of momentary exertion.

13. The method of claim 1, wherein the processing the oxygenation parameter generates the substantially real-time lactate curve which is a linear or non-linear function of one or more signal features.

14. A biosensor device comprising:
   a housing;
   an emitter disposed in the housing; the emitter configured to emit, at predetermined times, radiation into a tissue of a subject;
   a detector disposed in the housing, the detector being configured to detect, at corresponding predetermined times, a radiation emitted from a tissue of a subject and calculate a corresponding oxygenation parameter, at each of the corresponding predetermined times, of a tissue of the subject;
   a processor configured to process the oxygenation parameter to generate a substantially real-time lactate curve or ventilatory curve, which is based on one or more signal features of the oxygenation parameter and determine whether the lactate curve substantially contains a lactate threshold of the subject or the ventilatory curve substantially contains a ventilatory threshold of the subject; and
   a communication module configured to provide an alert based on the determination that the lactate curve contains a lactate threshold of the subject or the ventilatory curve substantially contains a ventilatory threshold of the subject;
   wherein the oxygenation parameter comprises at least one of concentration of oxygenated hemoglobin, and concentration of deoxygenated hemoglobin, total concentration of hemoglobin, and Tissue Oxygenation Index, and
   wherein the one or more signal features comprises:
   a first signal feature comprising a oxygenation parameter value during an exercise stage;
   a second signal feature comprising a change in the oxygenation parameter value;

a third signal feature comprising a rate of change in the oxygenation parameter value;

a fourth signal feature comprising a scale of change in the oxygenation parameter value.

15. The device of claim 14, wherein the processor is configured to analyze the one or more signal features in a signal profile of the oxygenation parameter.

16. The device of claim 15, wherein the signal feature is a characteristic in the signal profile.

17. The device of claim 15, wherein the signal feature is a linear model fit on a plateau interval of a curve of the oxygenation parameter.

18. The device of claim 15, wherein the signal feature is an amplitude of an exponential model of the oxygenation parameter.

19. The device of claim 15, wherein the signal feature is a time constant of an exponential model of the oxygenation parameter.

20. A biosensor system for measuring parameters of a subject during exercise, the system comprising:
the biosensor device comprising:
a housing;
an emitter disposed in the housing; the emitter configured to emit, at predetermined times, radiation into a tissue of a subject;
a detector disposed in the housing, the detector being configured to detect, at corresponding predetermined times, a radiation emitted from a tissue of a subject and calculate a corresponding oxygenation parameter, at each of corresponding times, of the tissue of the subject;
a secondary device comprising:
a receiver configured to receive data from the biosensor device;
a processor configured to process the data to generate a substantially real-time lactate curve or ventilatory curve, which is based on one or more signal features of the oxygenation parameter and determine whether the lactate curve substantially contains a lactate threshold of the subject or the ventilatory curve substantially contains a ventilatory threshold of the subject; and
a communication module configured to provide an alert based on the determination that the lactate curve contains a lactate threshold of the subject or the ventilatory curve substantially contains a ventilatory threshold of the subject;
wherein the oxygenation parameter comprises at least one of concentration of oxygenated hemoglobin, and concentration of deoxygenated hemoglobin, total concentration of hemoglobin, and Tissue Oxygenation Index, and
wherein the one or more signal features comprises:
a first signal feature comprising a oxygenation parameter value during an exercise stage;
a second signal feature comprising a change in the oxygenation parameter value;
a third signal feature comprising a rate of change in the oxygenation parameter value;
a fourth signal feature comprising a scale of change in the oxygenation parameter value.

21. The biosensor system of claim 20, wherein the biosensor device further comprises a second detector configured to measure photoplethysmography (PPT) of the subject; and a third detector configured to measure electrocardiography (EKG) and derived systolic time intervals (STI) of the subject; and the processor of the secondary device is further configured to analyze data generated by the detectors to determine a cardiac response to exercise and utilization of oxygen by the tissue.

22. The biosensor device of claim 21, wherein the second detector and the third detector are disposed in the housing.

* * * * *